(12) United States Patent
Konomura et al.

(10) Patent No.: US 6,793,622 B2
(45) Date of Patent: Sep. 21, 2004

(54) ELECTRIC BENDING ENDOSCOPE

(75) Inventors: Yutaka Konomura, Tachikawa (JP); Yasuo Hirata, Hachioji (JP); Takakazu Ishigami, Tama (JP)

(73) Assignee: Olympus Optical Co., Ltd., Tokyo (JP)

( * ) Notice: Subject to any disclaimer, the term of this patent is extended or adjusted under 35 U.S.C. 154(b) by 172 days.

(21) Appl. No.: 10/233,405

(22) Filed: Sep. 4, 2002

(65) Prior Publication Data

US 2003/0092965 A1 May 15, 2003

(30) Foreign Application Priority Data

| Sep. 5, 2001 | (JP) | 2001-269303 |
| May 17, 2002 | (JP) | 2002-143618 |
| Jun. 24, 2002 | (JP) | 2002-183266 |
| Jun. 24, 2002 | (JP) | 2002-183267 |

(51) Int. Cl.[7] ............................................. A61B 1/01
(52) U.S. Cl. ...................................... 600/152; 600/149
(58) Field of Search ................................ 600/146, 148, 600/149, 152

(56) References Cited

U.S. PATENT DOCUMENTS

| 4,499,895 A | | 2/1985 | Takayama | |
| 4,503,842 A | * | 3/1985 | Takayama | 600/152 |
| 4,721,099 A | * | 1/1988 | Chikama | 600/152 |
| 5,626,553 A | | 5/1997 | Frassica et al. | |
| 5,658,238 A | * | 8/1997 | Suzuki et al. | 600/150 |
| 5,667,476 A | | 9/1997 | Frassica et al. | |

FOREIGN PATENT DOCUMENTS

| JP | 56-48241 | 11/1981 |
| JP | 58-65132 | 4/1983 |
| JP | 63-5684 | 2/1988 |
| JP | 2-42246 | 11/1990 |

* cited by examiner

Primary Examiner—John P. Leubecker
(74) Attorney, Agent, or Firm—Dickstein, Shapiro, Morin & Oshinsky, LLP.

(57) ABSTRACT

An electric bending endoscope having a traction-member operating device according to the present invention has traction members each of whose one end portion is fixed to and extends from a distal end portion of a long and narrow inserting portion, a pulley forming multiple peripheral recesses in which middle parts of the traction members are wound and are located in predetermined states, respectively, a motor for rotating, in a predetermined direction, the pulley in the state where the traction members are wound and are located, an arm member having a plurality of arm members to which base end portions of the traction members wound and located in the peripheral recesses of the pulley and extended therefrom are fixed, and an operation instructing lever to which the arm member is integrally fixed and having an operating portion for changing a slanting direction and a slanting amount to instruct to move a predetermined traction member from the plurality of traction members by a predetermined amount.

12 Claims, 31 Drawing Sheets

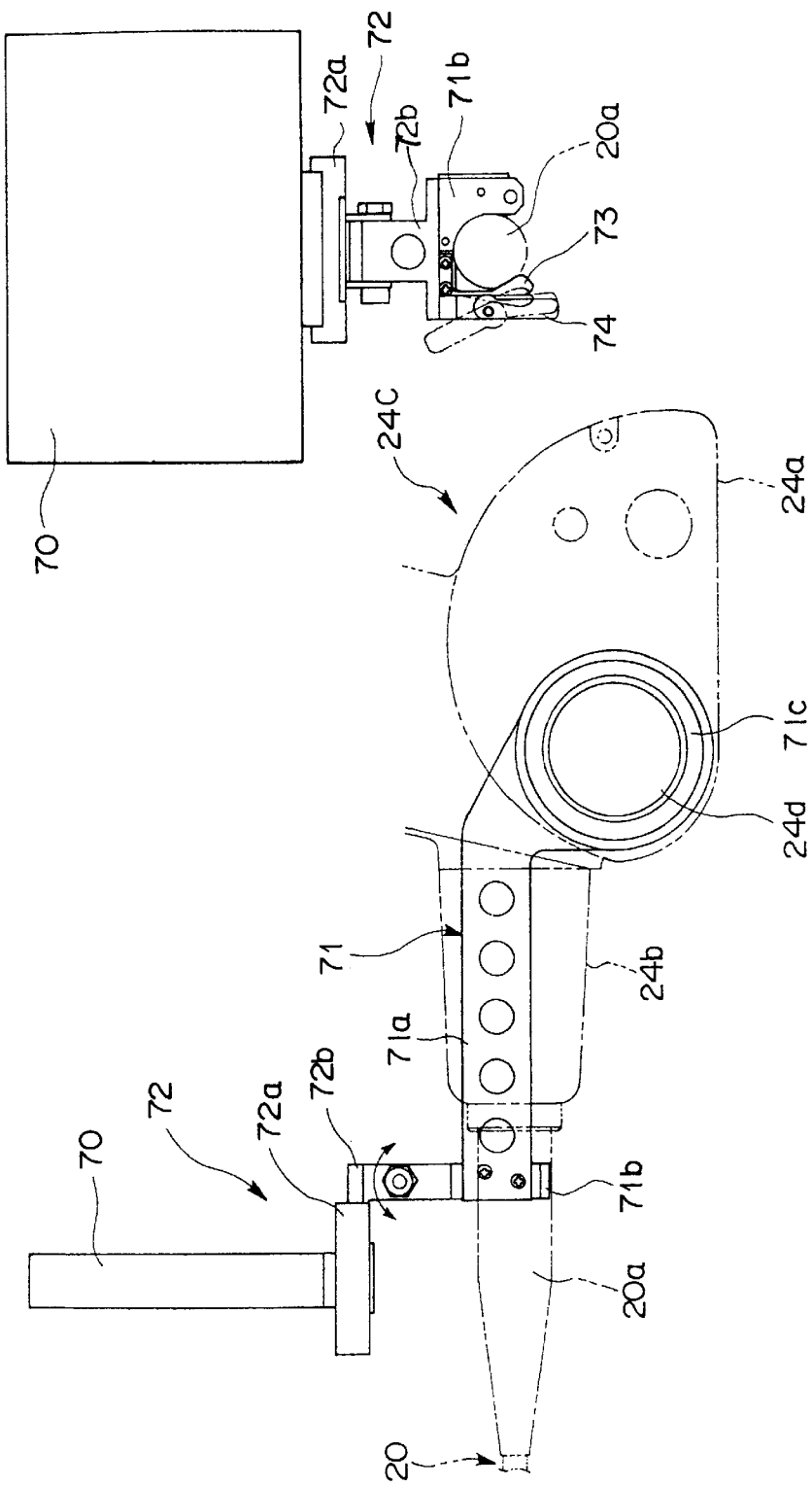

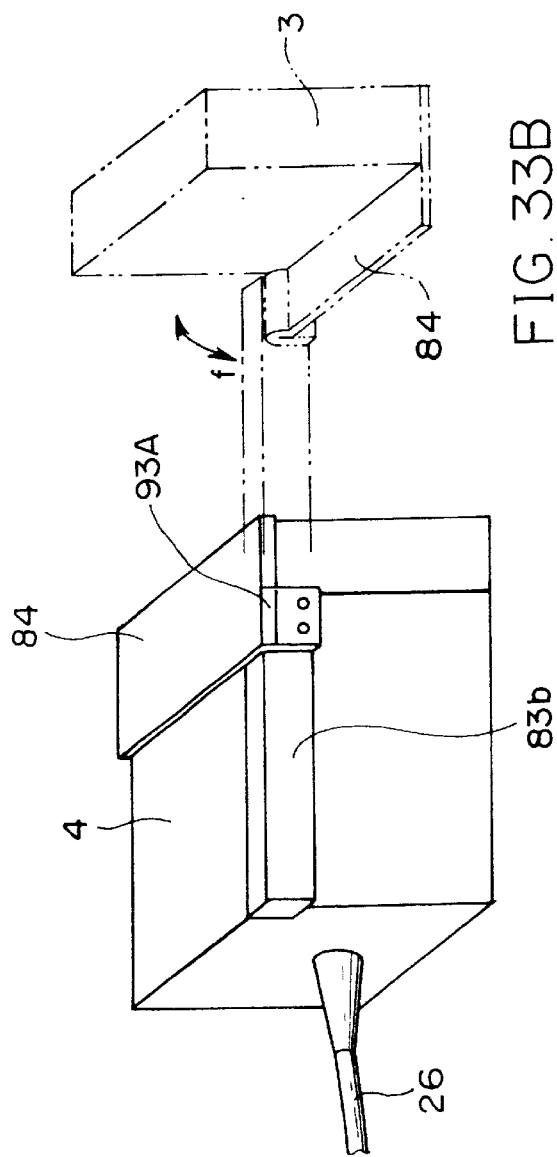
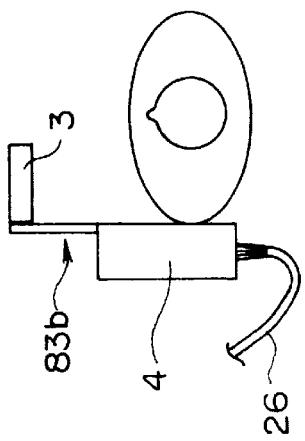
FIG. 33A
FIG. 33B

ELECTRIC BENDING ENDOSCOPE

This application claims benefit of Japanese Application Nos. 2001-269303 filed on Sep. 5, 2001, 2002-143618 filed on May 17, 2002, 2002-183266 filed on Jun. 24, 2002, 2002-183267 filed on Jun. 24, 2002, the contents of which are incorporated by this reference.

BACKGROUND OF THE INVENTION

1. Field of the Invention

The present invention relates to an electric bending endoscope for bending a bending portion provided in an inserting portion by moving a traction member by driving means.

2. Description of the Related Art

Conventionally, an endoscope has been widely used as an apparatus for observing and examining inside of a body cavity, tube or a gap in a construction and so on. This endoscope mainly includes an inserting portion to be inserted to a body cavity or a construction and an operating portion provided at the base end portion of the inserting portion. Some may have a bending portion provided to the inserting portion, which can be bent in the horizontal and vertical directions.

The bending portion performs a bending operation by moving back and forth a operating wire, not shown, which is a traction member inserting through the inside of the inserting portion. Thus, the distal end portion of the operating wire is fixed at the bending portion, and the base end portion is fixed at an operating wire attaching mechanism portion. The operating wire attaching mechanism portion is united with a single curving operating lever, which is an operation instructing lever provided in the operating portion. With this structure, by slantingly operating the curving operation lever, the corresponding operation wire is moved back and forth. Thus, the bending portion can be bent in a desired direction.

The endoscope having the structure in which the curving operation lever is slantingly operated to bend the bending portion as described above has advantages and disadvantages as follows: One of the advantages is that a bending operation in four directions, for example, can be performed by the single bending operation lever. On the other hand, one of the disadvantages is that the physical load on a user is too large. Since the bending operation lever is slantingly manipulated to tract a corresponding operation wire directly, the bending operation lever becomes heavier. In addition, significantly large force is required to maintain a bent condition of the bending portion.

In order to overcome the disadvantage, many endoscopes have been proposed which has a traction member operating device for reducing an amount of operating the bending operation lever and for increasing an amount of bending the bending portion.

For example, in a head bending apparatus disclosed in Japanese Examined Utility Model Registration Application Publication No. Sho 56-48241, two semicircular plates each of which is bent to a semicircular having a long recess are assembled such that the long recesses can cross at right angles. An operation lever is inserted to the crossed long recesses. In addition, shafts of both ends of both of the semicircular plates are rotatably supported by a stationary axis. A pivot is provided such that a semicircular rotation can be transmitted onto the extension of the stationary axis. The pivot is connected to a wire operation mechanism. Thus, bending operations in four directions can be performed by a single operation lever.

Furthermore, in a head bending device disclosed in the Japanese Examined Utility Model Registration Application Publication No. Sho 63-5684, two semicircular plates each of which is bent to a semicircular having a long recess are assembled such that the long recesses can cross at right angles. In the bending device in which an operating lever is inserted through the crossed long recesses, a shaft of one end portion of the semicircular plate is supported by a bearing. The other end portion is connected to multiple planetary gears engaging with an internal teeth, which is formed within an angle drum winded with an angle operation wire. Thus, an amount of the wire movement is increased.

Furthermore, in an endoscope disclosed in Japanese Examined Utility Model Registration Application Publication No. Hei 2-42246, a hydropneumatic cylinder is provided in an operation body. A piston rod of the hydropneumatic cylinder is linked to a pulley, which is rotator supported by the operation body. A banding portion is bent through an operation wire linked to the pulley so as to reduce an amount of operation force.

Furthermore, an endoscope disclosed in Japanese Unexamined Patent Application Publication No. Sho 58-65132 includes a motor for driving a distal end bending mechanism, a bending operation member provided in an operation portion for receiving operation force manually, a detecting unit for detecting an amount of operation force received by the bending operation member and a control unit for processing a signal obtained by the detection unit and for controlling driving electric power to the motor. Thus, the amount of operation force is detected so as to drive the motor.

However, the methods for bending a bending portion as disclosed in the Japanese Examined Utility Model Registration Application Publication No. Sho 56-48241, Japanese Examined Utility Model Registration Application Publication No. Sho 63-5684, Japanese Examined Utility Model Registration Application Publication No. Hei 2-42246 are complicated in the construction. Thus, there is a disadvantage that the form becomes larger. In addition, since the more an amount of moving a wire for bending the bending portion is increased, the more the amount of operation is increased. Thus, it is not practical.

In the bending method of the bending portion disclosed in the Japanese Examined Utility Model Registration Application Publication No. Sho 58-65132, an amount of operation is detected, and a motor is driven in accordance with the detected amount of operation. Thus, a control circuit is required, which complicates the structure.

In addition, when a hand holding the operating portion is frequently lifted in handling the endoscope, a load is put on an arm supporting the endoscope. Thus, it is likely that the operability is reduced with the passage of time.

On the other hand, the endoscope needs a light source for illuminating an observed subject since a diagnosed or examined subject is in a living body, a plant or the like. Therefore, a light source device is prepared as an external device of the endoscope.

When the endoscope is optical, an end surface of an image guide is located at an image forming position of an observation optical system. Then, the formed image is transmitted to the base end side of the inserting portion through the image guide. Thus, a user can observe an endoscope-observed part under magnification through an eyepiece. As a result, an endoscope apparatus can be constructed which is excellent in mobility by having a battery, such as a dry battery and a chargeable battery, as a power source of the light source device. Therefore, the use in a place into which carrying a large light source device is difficult or a place where a commercial power source cannot be obtained becomes possible. Especially, an excellent effect can be shown in an emergency.

However, when an endoscope is electronic, an image pickup element such as charge coupled device (CCD) is located at an image-forming position, and an optical image is optoelectronic-transduced to image signals. The image signals output from the image pickup element are signal-processed in a video processing device to create video signals. The video signals are output to a monitor device. Thus, an image of the endoscope-observed part is displayed on a screen to perform an observation thereof.

In other words, when an examination is performed by using the electronic endoscope, the video processing device and a monitor device are required in addition to the combination of an endoscope and an optical source device, which is a construction of the optical endoscope apparatus. Therefore, it is difficult to construct an endoscope as a mobile device.

SUMMARY OF THE INVENTION

It is an object of the present invention to provide an electric bending endoscope excellent in operability in that a desired traction member is moved by a desired amount to bend a bending portion by slantingly operating an operation instructing lever with a small amount of operation force.

It is another object of the present invention to provide an electric bending endoscope excellence in grasp and operability in that a load onto an arm of a user grasping the endoscope is reduced and a twisting operation of an inserting portion and/or a bending operation of a bending portion can be performed freely.

It is another object of the present invention to provide an electric bending endoscope excellent in workability and mobility by using a battery such as a dry battery and a chargeable battery as a power source of each of an electric bending endoscope, light source device, a video processing device and a monitor.

An electric bending endoscope having a traction-member operating device according to the present invention has traction members each of whose one end portion is fixed to and extends from a distal end portion of a long and narrow inserting portion, a pulley forming multiple peripheral recesses in which middle parts of the traction members are wound and are located in predetermined states, respectively, a motor for rotating, in a predetermined direction, the pulley in the state where the traction members are wound and are located, an arm member having a plurality of arm members to which base end portions of the traction members wound and located in the peripheral recesses of the pulley and extended therefrom are fixed, and an operation instructing lever to which the arm member is integrally fixed and having an operating portion for changing a slanting direction and a slanting amount to instruct to move a predetermined traction member from the plurality of traction members by a predetermined amount. Therefore, a load on a user is reduced, and the operability and the workability are improved.

The above and other objects, features and advantages of the invention will become more clearly understood from the following description referring to the accompanying drawings.

BRIEF DESCRIPTION OF THE DRAWINGS

FIG. 19A is a diagram viewing, from the side, an operating portion to which a liquid crystal monitor is mounted;

FIG. 19B is a diagram viewing, from the front side, an operating portion to which a liquid crystal monitor is mounted;

FIG. 33A is a diagram for explaining another construction of a display-device positioning member; and FIG. 33B is a diagram for explaining a state where the display-device positioning member is used.

DETAILED DESCRIPTION OF PREFERRED EMBODIMENTS

An endoscope apparatus having an electric bending endoscope relating to a first embodiment of the present invention will be described with reference to FIGS. 1 to 10.

Figure 1:
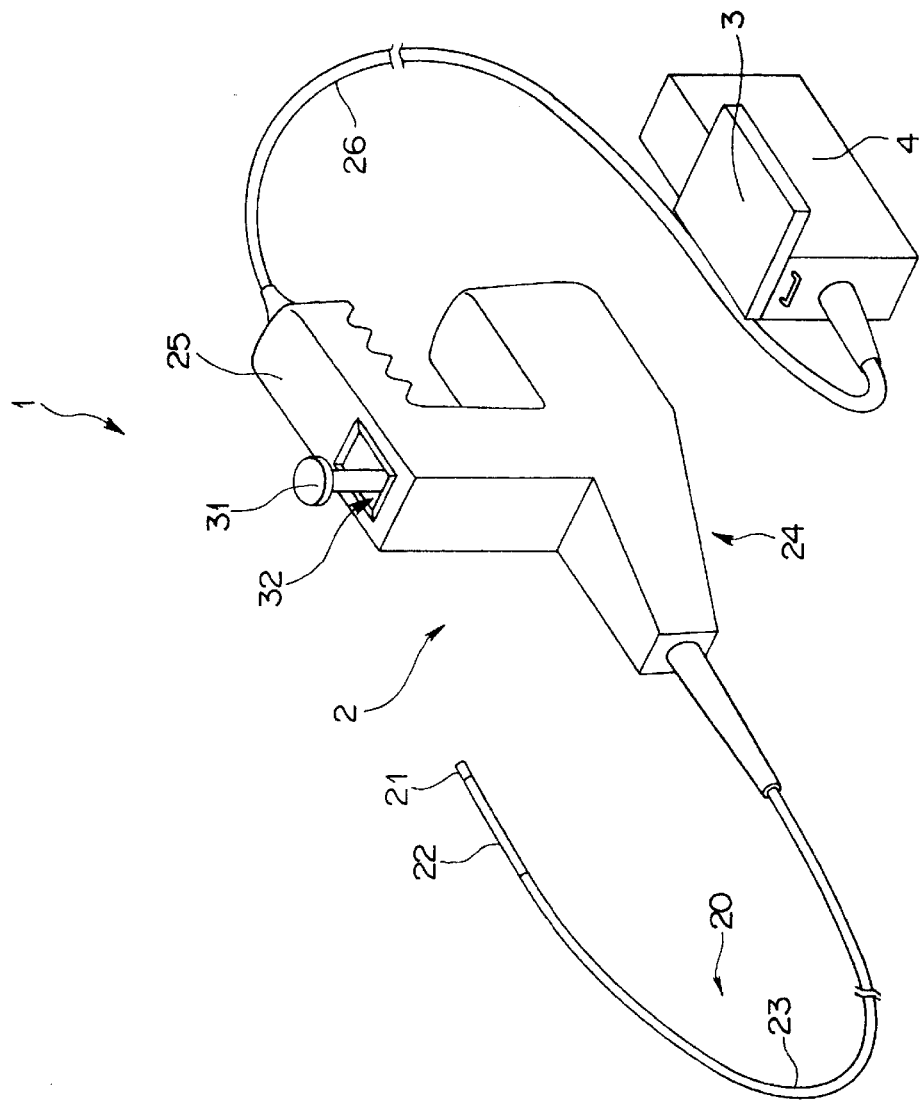
FIG. 1 is a diagram for explaining an electric bending endoscope including a traction member operating device of the present invention.

As shown in FIG. 1, an endoscope apparatus 1 of this embodiment mainly includes an industrial, for example, electric bending endoscope (abbreviated as endoscope, hereinafter) 2 and an apparatus body 4 having a monitor 3, which is a display device for displaying an endoscope image.

The endoscope 2 self-contains an image pickup element (not shown) in a distal end portion 21 of an inserting portion 20. The apparatus body 4 is provided with a light source portion for supplying illuminating light for illuminating a observed part, an image processing portion for driving the image pickup element and for generating a video signal from an image signal output from the image pickup element, and a battery for supplying electric power, for example. The monitor receives a video signal output from the image processing portion and displays an endoscope image. Therefore, the endoscope 2 in this embodiment is of a battery-driven type.

The endoscope 2 includes an inserting portion 20, an operating portion 24, and a universal cord 26. The inserting portion 20 is long and narrow and has flexibility. The operating portion 24 is linked to a base end part of the inserting portion 20. The universal cord 26 has flexibility and extends from the operating portion 24.

A light guide fiber (not shown), a signal cable (not shown) and so on are inserted through the universal cord 26. The light guide fiber supplies illuminating light. The signal cable transmits a drive control signal for an image pickup element or an image signal photoelectrically transduced by the image pickup element.

The inserting portion 20 includes a distal end portion 21, a bending portion 22, and a flexible tube portion 23 from the distal side in that order. The bending portion 22 is constructed so as to bend in the vertical/horizontal directions, for example by installing a bending piece, described later, consecutively. The flexible tube portion 23 has flexibility. An observation window, an illumination window, a forceps conducting port, a injection nozzle for conducting water and/or air and so on, which are not shown, are provided on a distal end surface of the distal end portion 21.

The operating portion 24 is constructed in a substantial h-form. A grasping portion 25 of an axis different from an inserting axis of the inserting portion 20 is provided in the operating portion 24. A bending-operation instructing lever (abbreviated as a bending lever, hereinafter) 31, which is an operation instructing lever for bending the bending portion 22 is provided on the distal end side of the grasping portion 25. The bending lever 31 projects from an opening portion 32. The universal cord 26 extends from the base end portion of the grasping portion 25 and has the other end electrically connected to the apparatus body 4.

The bending lever 31 performs a slanting operation, which changes a slanting direction and a slanting angle, and bends the bending portion 22 by an desired bending amount in a desired direction by moving a traction member, which will be described later. Then, it is arranged in advance such that the bending portion 22 can be in a straight-line state when the bending lever 31 is in upright stance.

Figure 2:
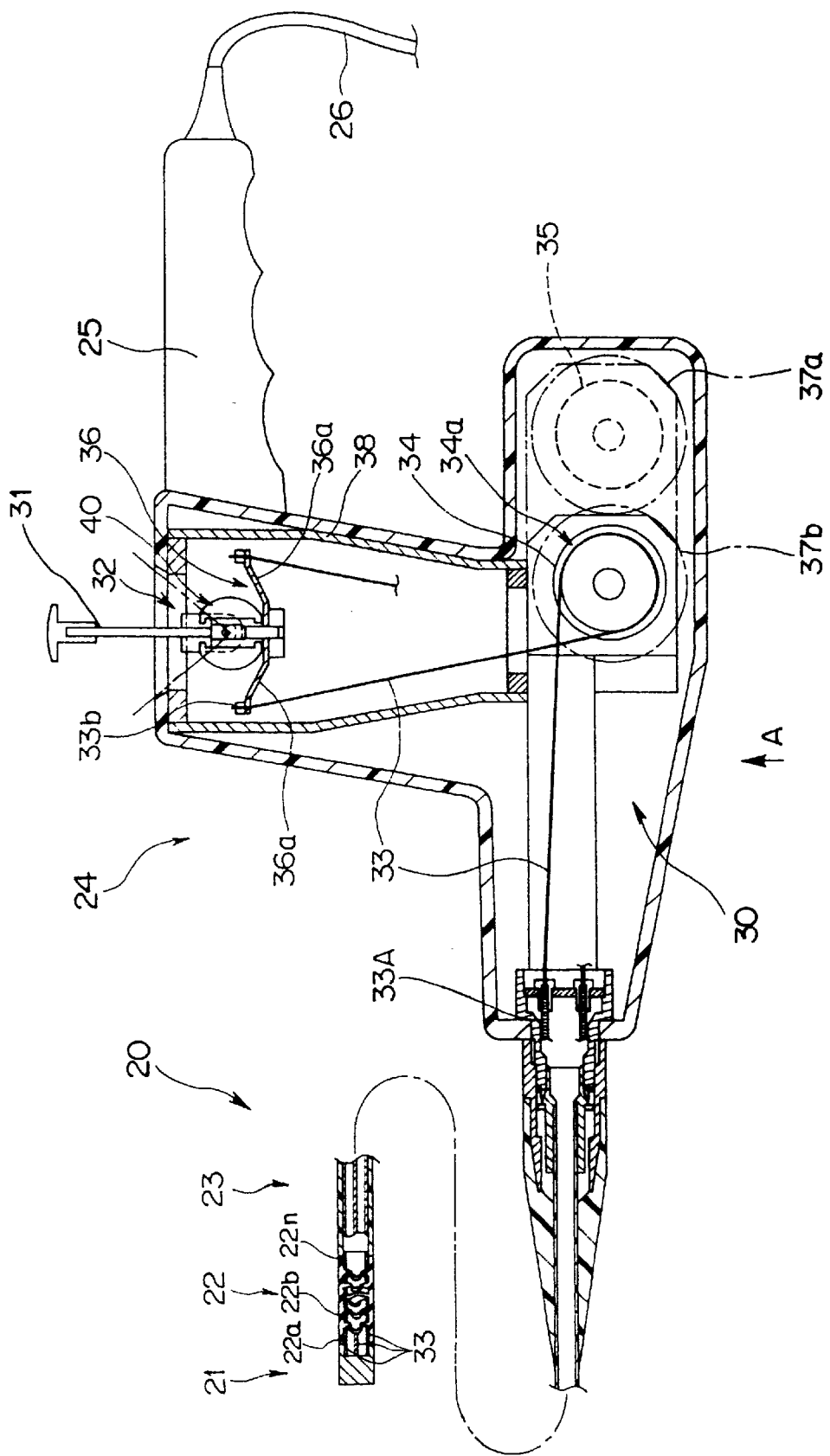
FIG. 2 is a longitudinal section diagram for explaining a bending device, which is the traction member operating device provided in the electric bending endoscope.

As shown in FIG. 2, the bending portion 22 is constructed by installing multiple bending pieces 22a, . . . and 22n consecutively. The most distal end bending piece 22a constructing the bending portion 22 is linked to a distal end hard member 21a constructing the distal end portion 21. Distal end portions of four operating wires 33, which are traction members corresponding to the up and down and right and left operating directions constructing the bending device 30 are fixed in a predetermined positions of the most distal end bending piece 22a.

Figure 3:
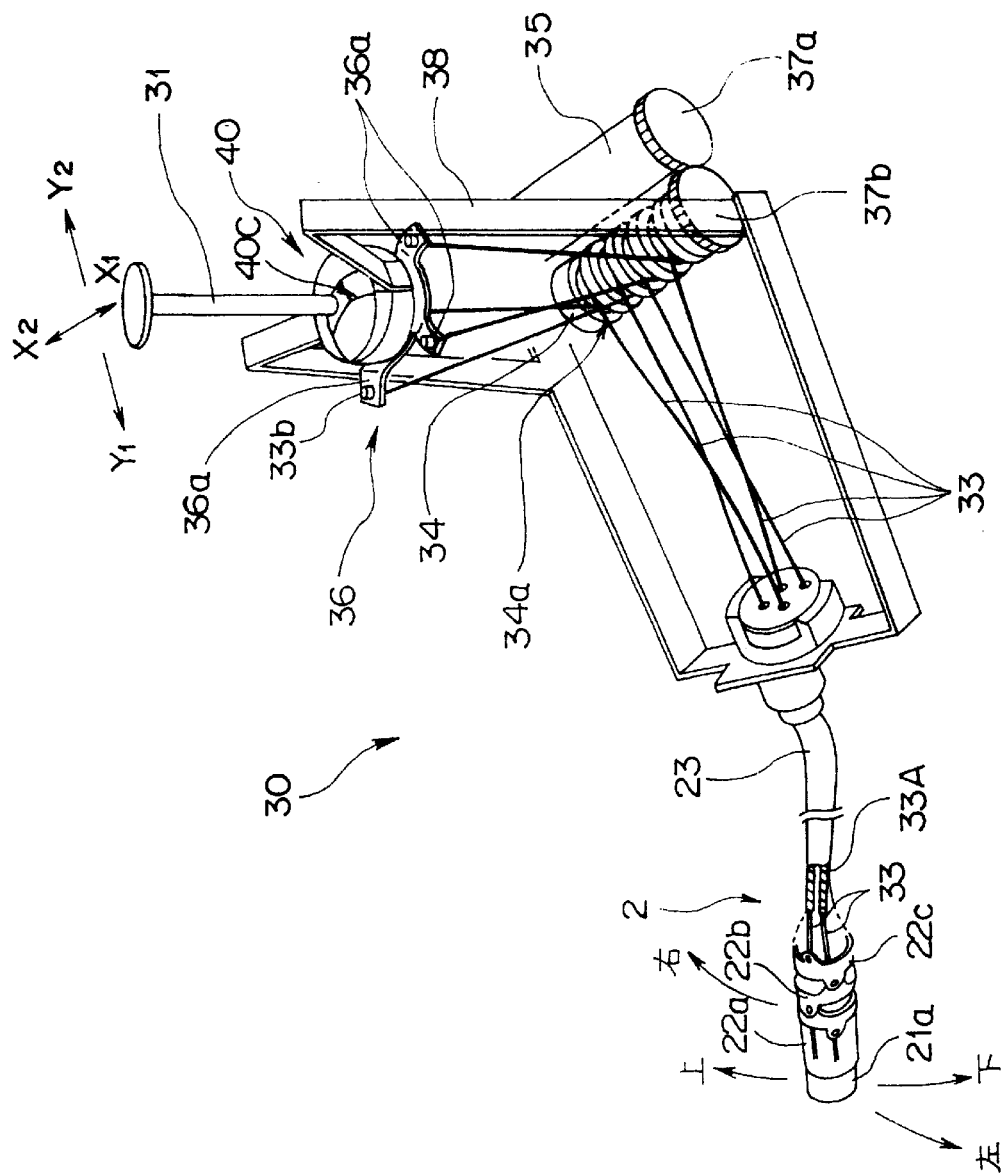
FIG. 3 is a diagram for explaining an essential part of the bending device.
Figure 4:
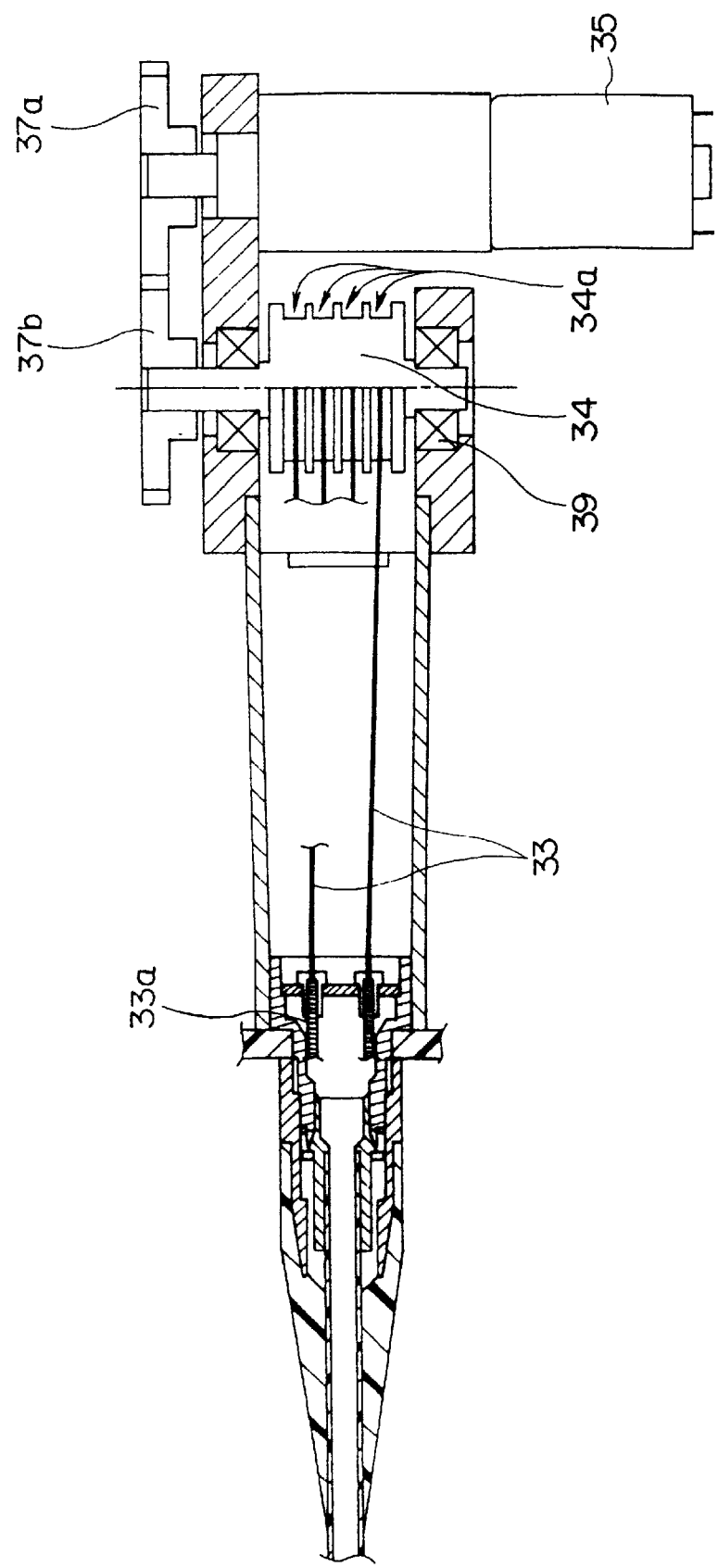
FIG. 4 is a diagram for explaining the bending device viewed from a direction indicated by an arrow A in FIG. 2.

As shown in FIGS. 2 to 4, the bending device 30, which is a traction-member operating device of this embodiment, mainly includes the operating wire 33, a pulley 34, a motor 35, which is a driving unit, and a substantial-cross shape arm member 36. A peripheral recess 34a around which the middle parts of the operating wires 33 are wound is formed in the pulley 34. The motor 35 rotates the pulley 34 by using predetermined torque in a predetermined direction. The arm member 36 is integrated with the bending lever 31, and the base end portions of the operating wires 33 are fixed at predetermined positions, respectively.

The operating wires 33 are inserted through the inside a wire-inserted pipeline 33A inserted through the inside of the inserting portion 20 and extends to the inside of the operating portion 24. Then, the operating wires 33 wind around the pulley 34. A predetermined bent-form arm portion 36a is provided to the arm portion 36. The base end portion of the operating wires 33 are integrally fixed to the arm portion 36a through a wire fixture 33b.

The pulley 34 is adjusted to rotate by a first gear 37a and a second gear 37b for transmitting drive force from the motor 35. The middle parts of the operating wires 33 are wound around the peripheral recess 34a formed in the pulley 34 in a predetermined loose state.

The bending lever 31 and the arm member 36 are mounted and fixed to a bending frame 38 coaxially at a predetermined position facing against a bearing 40, which will be described later, provided rotatably. A reference numeral 39 is a bearing for supporting the pulley 34 rotatably.

Figure 5:
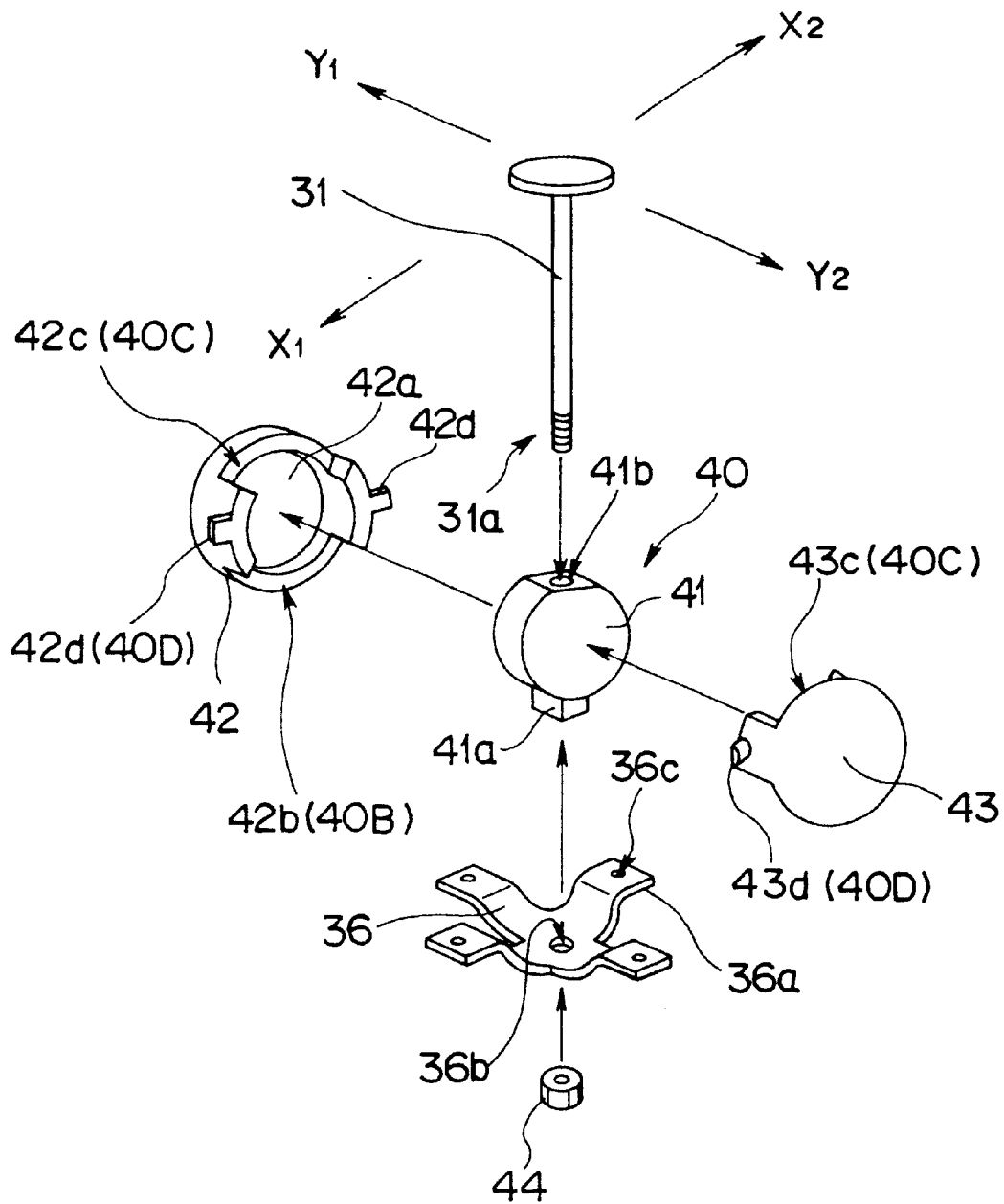
FIG. 5 is a diagram for specifically explaining a construction of a bearing.

As shown in FIG. 5, the bearing 40 mainly includes a circular axis 41 and a pair of sphere bearing 42 and 43. The circular axis 41 is formed in a substantial cylinder form. A convex arm member fixing portion 41a is provided to a part of the peripheral surface of the circular axis 41. A through-hole 41b through which the bending lever 31 is inserted is formed in the arm member fixing portion 41a.

Therefore, by performing the assembly in accordance with following steps, the arm member 36 and the bending lever 31 are fixed to the circular axis 41 coaxially. First of all, the bending lever 31 is inserted through the through-hole 41b. Next, a filtering hole 36b provided at a center part of the arm member 36 is inserted through the distal end portion of the bending lever 31 under the state. Next, a fixing nut 44 is screwed with a screw portion 31a of the bending lever 31.

The first sphere beating 42 and the second sphere bearing 43 are formed in a semi-sphere form dividing a sphere member into two. Circular bearing portions 42a and 43a with which the circular axis 41 is engaged are formed within the divided semi-sphere forms, respectively. The circular bearing portion 43a is not shown in FIG. 5 because of the composition.

A notch portion 42b for the fixing-portion and a notch portion 42c for positioning the lever are formed in the first sphere bearing 42. On the other hand, a notch portion 43b for the fixing portion and the notch portion 42c for positioning the lever are formed in the second sphere bearing 43. The notch portion 42b for the fixing portion and the notch portion 42c for positioning the lever and the notch portion 43b for the fixing portion and the notch portion 42c for positioning the lever are formed by facing each other.

Therefore, by forming the first sphere bearing 42 and the second sphere bearing 43 integrally, the notch portions 42b and 43b for the fixing portion are formed integrally to construct a recess portion 40B for the fixing portion. In addition, the notch portions 42c and 43c for positioning the lever are formed integrally to construct a recess portion 40C for the lever. The arm member fixing portion 41a is placed in the recess portion 40B for the fixing portion, and the bending lever 31 is placed in the recess portion 40C for the lever. The notch portion 42c for positioning the lever is not shown in FIG. 2 because of the composition.

In addition, a pair of semi-cylinder portions 42d and 43d, which form an axis portion 40D when integrated, are provided in the first sphere bearing 42 and the second sphere bearing 43 coaxially.

A reference numeral 36c is a wire fixing hole through which the operation wires 33 are inserted.

The bearing 40 is formed by holding the circular axis 41 between the first sphere bearing 42 and the second sphere bearing 43 rotatably. The arm member 36 and the bending lever 31 are mounted and fixed to the circular axis 41 coaxially. Therefore, by rotating the circular axis 41 in the ranges of the recess portions 40B and 40C, the bending lever 31 is constructed swingably in a direction indicated by an arrow X1 and in a direction indicated by an arrow X2.

On the other hand, the axis portion 40D formed by integrating the semi-cylinder portions 42d and 43d when the first sphere bearing 42 and the second sphere bearing 43 are integrated is located at a predetermined position of the bending frame 38 rotatably. Thus, the bearing 40 can rotate with respect to the axis portion 40D. As a result, the bending lever 31 has a swingable construction in a direction indicated by an arrow Y1 and in a direction indicated by an arrow Y2.

In this way, by manipulating the bending lever 31 in the direction indicated by the arrow X1 or the direction indicated by the arrow X2 or the direction indicated by the arrow Y1 or the direction indicated by the arrow Y2, the arm member 36 swings in response to the slanting operation of the bending lever 31.

The bending lever 31 is put in upright stance as shown in FIG. 3. Then, the base end portions of the four operation wires 33 are fixed to the wire fixing holes 36c, respectively of the arm member 36. Here, all of pulley rear side portions of the operating wires 33 winding the peripheral recess 34a of the pulley 34 in a predetermined condition and extending to the arm member 36 side are in a predetermined loose condition.

Therefore, by slanting the bending lever 31, the tension of the pulley rear side portions of the operation wire 33 fixed at the wire fixing hole 36c of the arm portion 36a corresponding to the slanting direction of the bending lever 31 is changed from the loose condition to the pulled condition. Then, the drag from the operating wire 33 to the peripheral recess 34a of the pulley 34 is increased. As a result, the resistance between the operating wire 33 and the pulley 34 is increased.

On the other hand, the other operating wires 33 are more loosened.

Figure 6:
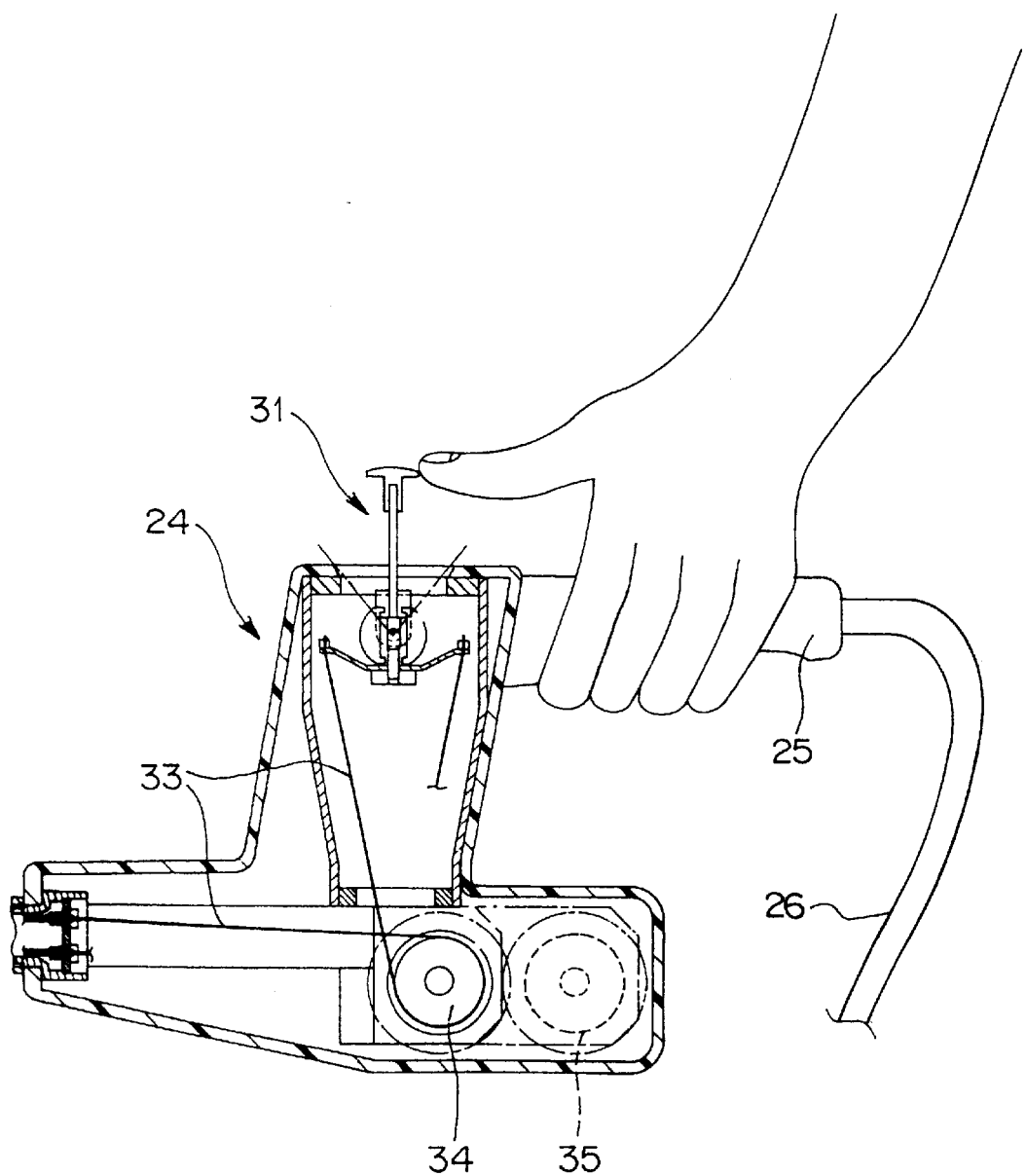
FIG. 6 is a diagram for explaining an operating condition of the bending device.

By constructing the endoscope 2 in this way, the grasping portion 25 can be grasped with leaving the arm down as shown in FIG. 6. In addition, the bending lever 31 can be manipulated freely with the thumb of the hand grasping the grasping portion 25. Therefore, the twisting operation of the inserting portion 20 and the bending operation on the bending portion 22 can be performed freely without putting load on the arm.

Figures 7A, 7B:
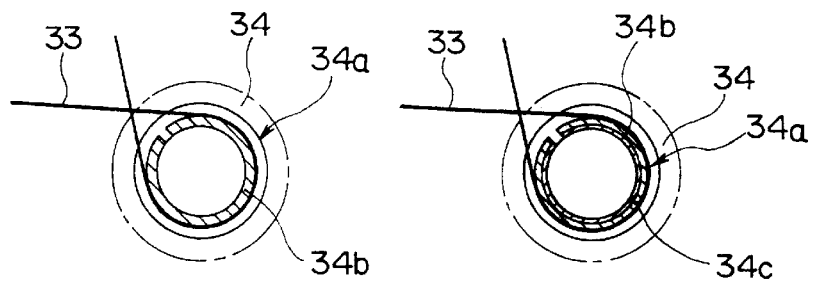
FIG. 7A is a diagram for explaining one construction example of an operation wire and a pulley.
FIG. 7B is a diagram for explaining another construction example of an operation wire and a pulley.
Figure 7C:
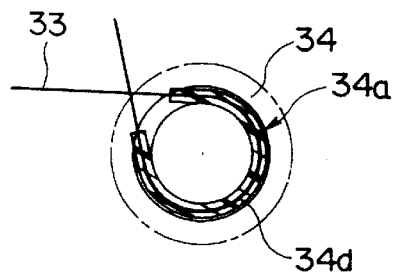
FIG. 7C is a diagram for explaining still another construction example of an operation wire and a pulley.
Figure 7D:
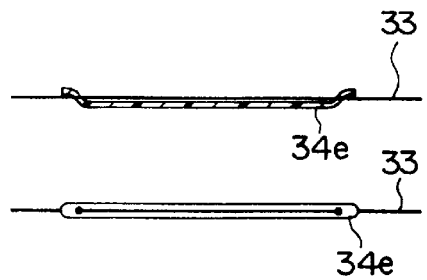
FIG. 7D is a diagram for explaining an example of placing a friction member in the operation wire.
Figure 7E:
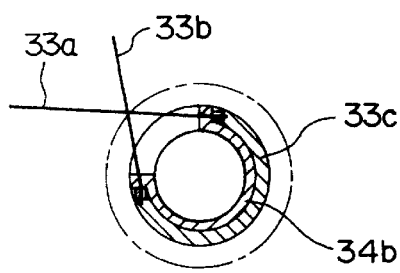
FIG. 7E is a diagram for explaining another construction example of a traction member.

In the above-described construction, the bending wires 33 are directly located at the peripheral recess 34a formed in the pulley 34. However, the operating wires 33 may be located in a C-ring 34b, which is a buffer member with a predetermined hardness located in the pulley 34 rotatably, as shown in FIG. 7A. A friction plate 34c with a predetermined friction coefficient may be placed between the C-ring 34b and the pulley 34 as shown in FIG. 7B such that a rotational force can be transmitted from the C-ring 34b to the operation wires 33. A friction member 34d may cover the operation wires 33 integrally as shown in FIG. 7C. A friction member 34e may be located and fixed to the operating wire 33 integrally and the friction members 34d and 34e may be located at the peripheral recess 34a provided in the pulley 34 as shown in FIG. 7D. A traction member may be formed by two operation wires 33a and 33b and a connecting member 33c so that the linking member 33c can be located to the C-ring 34b located in the peripheral recess 34a provided in the pulley 34.

These constructions can prevent the operation wires 33 and the pulley 34 from contacting with each other directly. Thus, a problem that the pulley 34, which rotates at all times, is scraped off by the operation wires 33 and the surface condition is changed and force amount is changed and/or, conversely, a problem that the operating wires 33 are worn by the pulley 34, which rotates at all times, and are broken, can be prevented.

Figure 8A:
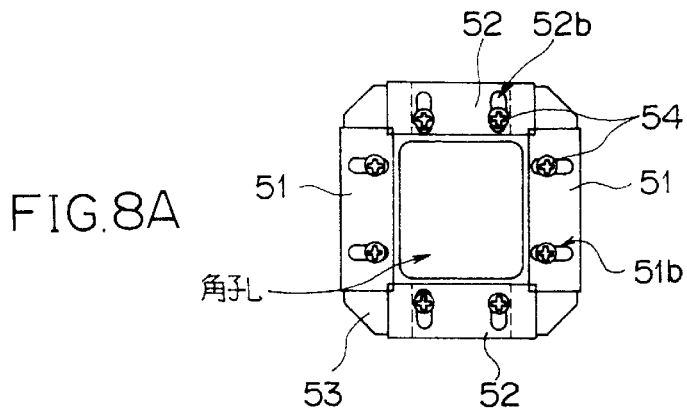
FIG. 8A is a diagram viewing, from the above, a slanted adjusting portion for adjusting a maximum slanting operation range of a bending lever.
Figure 8B:
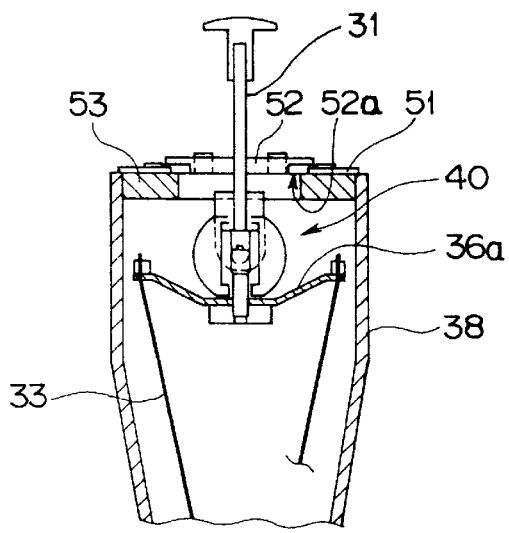
FIG. 8B is a sectional side elevation for explaining a slanted adjusting portion for adjusting a maximum slanting operation range of a bending lever.

A pair of a first slanting state adjusting member 51 and a second slanting state adjusting member 52 for adjusting a maximum slanting operation range of the bending lever 31 may be provided in an opening 32 from which the bending lever 31 is projected as shown in FIGS. 8A and 8B. Thus, the slanting operation range of the bending lever 31 may be adjusted properly.

The first slanting state adjusting member 51 is a flat plate member. On the other hand, the second slanting state adjusting member 52 is a member with steps including an escape portion 52a for the first slanting state adjusting member 51 formed by the flat plate member. The first slanting state adjusting member 51 and the second slanting state adjusting member 52 are screwed and are fixed with screws 54 into a plate 53 having a rectangular hole (abbreviated as plate, hereinafter) integrally fixed to the bending frame 38.

Figure 8C:
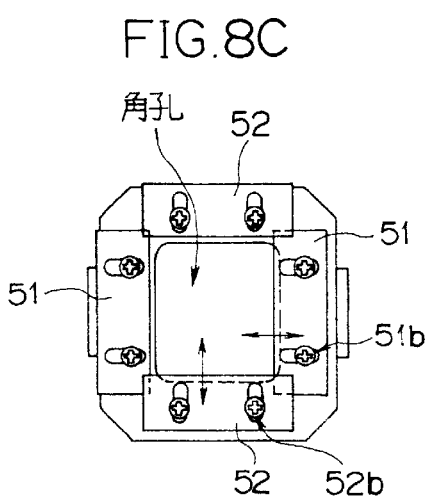
FIG. 8C is a diagram for explaining an action of each of members included in the slanted adjusting portion.

A female screw portion (not shown) is formed in a predetermined position of the plate 53. On the other hand, long holes 51b and 52b corresponding to the screws 54 are provided to the first slanting state adjusting member 51 and the second slanting state adjusting member 52. Therefore, as shown in FIG. 8C, the first slanting state adjusting member 51 and the second slanting state adjusting member 52 can move so as to change the size of the rectangular hole formed in the plate 53 as shown in FIG. 8C.

Figure 8D:
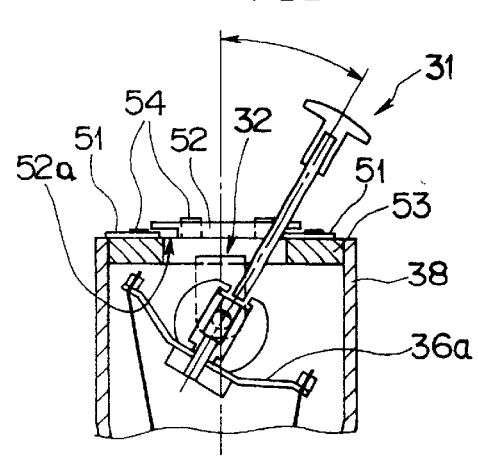
FIG. 8D is a diagram for explaining an example of a maximum slanting operation state of the bending lever.

Therefore, by moving the first slanting state adjusting member 51 to the center side, for example, the rectangular hole formed in the plate 53 becomes smaller as shown in FIG. 8D. In other words, when the bending lever 31 is slanted, the bending lever is abutted against the first slanting state adjusting member 51. That is, the maximum slanting operation range of the bending lever 31 becomes smaller than being abutted against the rectangular hole formed in the plate 53.

In this way, by locating, at a predetermined position, the pair of the first slanting state adjusting member 51 and the second slanting state adjusting member 52, which is movable with respect to the plate 53 having the rectangular hole, the slanting operation range of the bending lever can be adjusted properly by moving it in a direction decreasing the size of the rectangular hole formed in the plate 53 having the rectangular hole.

Here, the relationship between the operation of the bending lever 31 and the bending portion 22 will be described.

Figure 9:
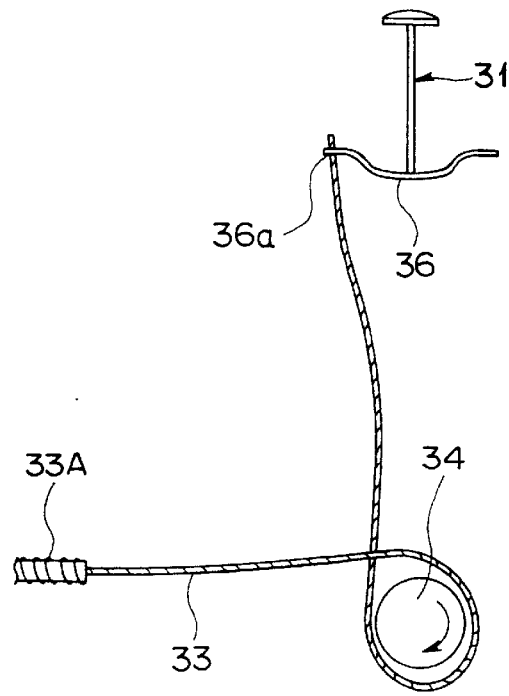
FIG. 9 is a diagram showing a state where the traction member of the bending device is wound in a predetermined loose state.

In order to bend the bending portion 22 by performing a bending operation on the bending lever 31, the pulley 34 is rotated by driving the motor 35 in advance. Here, when the bending lever 31 is in upright stance, all of the operating wires 33 winding around the pulley 34 as shown in FIG. 9 are loosened at a predetermined degree. Thus, all of the operation wires 33 can slide around the pulley 34. Thus, the bending state of the bending portion 22 is maintained in the straight line state.

When the bending portion 22 is bent upward, for example, the bending lever 31 shown in FIG. 3 is slanted in the direction indicated by the arrow Y2. Then, in response to the slanting operation of the bending lever 31, the bearing 40 rotates with respect to the axis portion 40D. As a result, the arm member 36 is slanted. Thus, a part located in the more base end side, with respect to the pulley 34, of the operation wire 33 for the up direction, which is fixed to the wire fixing hole 36c of the arm portion 36a corresponding to the slanting direction of the bending lever 31 is changed from the predetermined loose state to the pulled state gradually. Here, the other operation wires 33 corresponding to the down, left and right directions are changed to a more loose state.

Thus, only the drag of the operation wire 33 for the up direction against the pulley 34 is increased among the operation wires 33 winding the peripheral recess 34a of the pulley 34 in the predetermined loose state. That is, the resistance value between the operation wire 33 for the up direction and the pulley 34 is increased.

Figure 10:
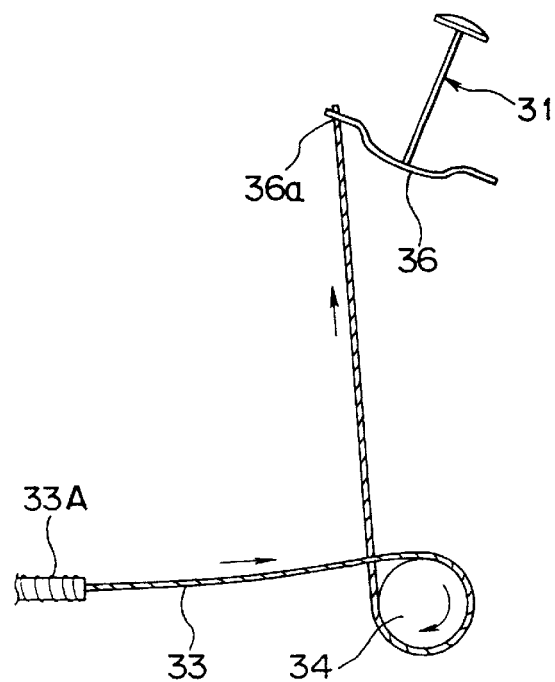
FIG. 10 is a diagram showing a state where the traction member of the bending device is moved by the rotation of the pulley.
Figure 11:
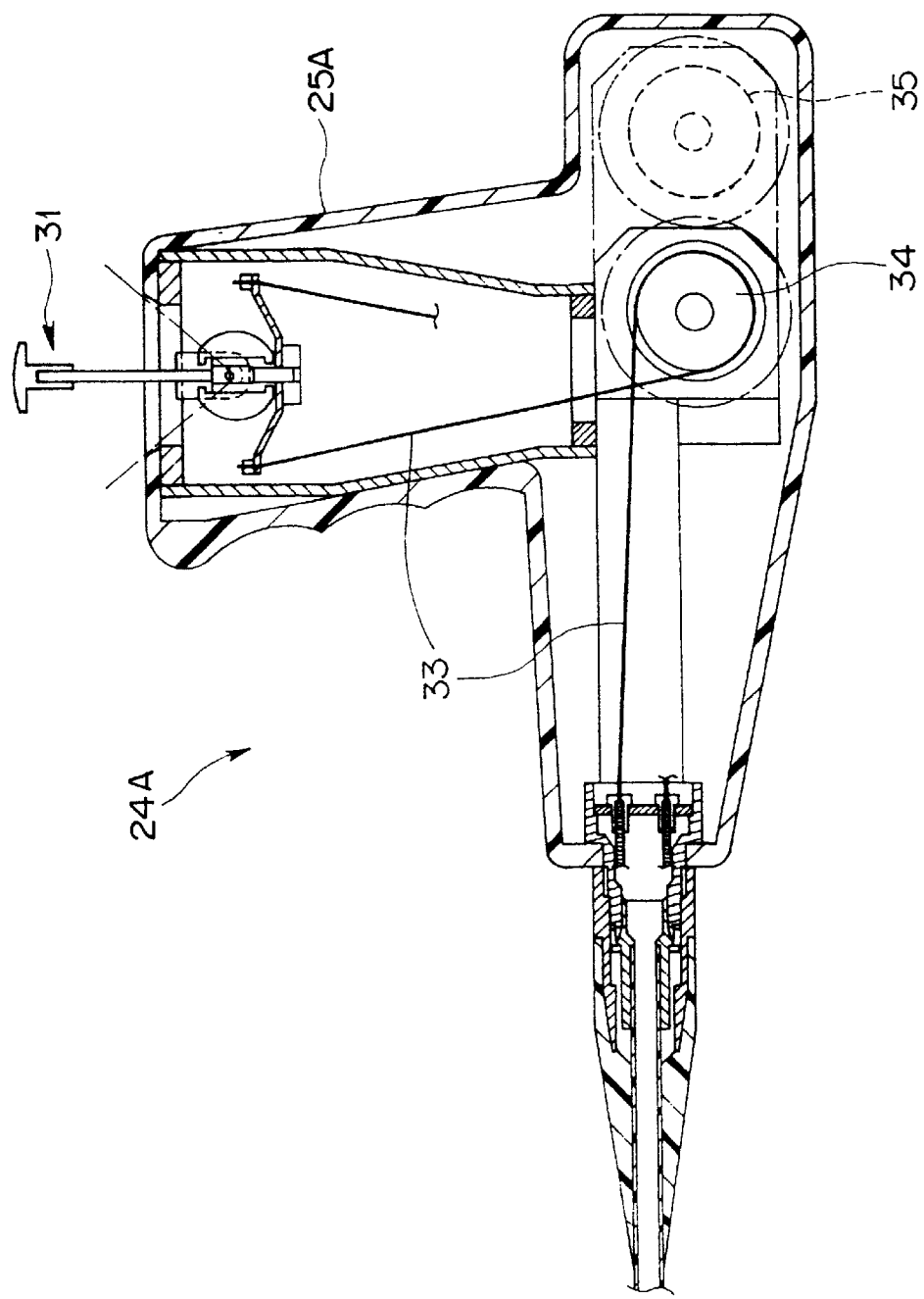
FIG. 11 is a diagram for explaining another construction of an operating portion.

Then, due to the increase in the resistance between the operation wire 33 for the up direction and the pulley 34, the rotational force of the pulley 34, which is rotated by the motor 35 as shown in FIG. 10, is transmitted to the operation wire 33. Then, the operation wire 33 moves as indicated by an arrow with respect to the rotational direction.

Therefore, in this embodiment, the operation wire 33 for the up direction located at the more distal end side with respect to the pulley 34 is pulled and is moved to the arm portion 36a side, and the bending portion 22 starts the bending operation in the up direction.

Under this state, in order to increase the drag of the operation wire 33 for the up direction against the pulley 34, the bending lever 31 is continuously slanted in the same direction. Then, the operation wire 33 located in the more distal end side with respect to the pulley 34 is further pulled and is moved. Thus, the bending portion 22 is further bent in the up-direction.

On the other hand, when the slanting position of the bending lever 31 is continuously maintained, the drag of the operation wire 33 against the pulley 34 is reduced gradually with the movement of the operation wire 33 located in the more distal end side with respect to the pulley 34. Thus, the movement stops under a condition where a pulling force is caused on the operation wire 33 located in the more distal end side with respect to the pulley 34. Here, the other operation wires 33 than the operation wire 33 corresponding to the bending direction is loose. Then, by continuously maintaining the bending lever 31 under this state, the state of the operation wire 33 is maintained as it is. That is, the bending state of the bending portion 22 is maintained.

In order to bend the bending portion 22 in the same direction further, to bend it in another direction or to return it to the original state, the bending lever 31 is slanted in a desired direction. Thus, the drag of the operation wire 33 corresponding to the slanting operation against the pulley 34 is changed. As a result, the corresponding operation wire 33 is moved and the bending portion 22 is changed into the bending state corresponding to the slanting operation of the bending lever 31.

In this way, the operation wires, which correspond to the up and down and right and left loosely winding around and extended from the pulley being rotated in a predetermined direction by a motor, is fixed to the arm portion of an arm member arranged to swing in accordance with a slanting operation on the bending lever for instructing to bend the bending portion in the up or down/right or left direction. Then, the bending lever is slanted so that the pulling state of the operation wire corresponding to the slanting operation, which is fixed to the arm member, is changed. As a result, the drag of the corresponding operation wire against the pulley is changed. Thus, the operation wire is moved in the direction of rotating the pulley so that the bending portion can be bent.

The amount of holding force is reduced from the state where the bending lever is slanted. Thus, the pulled operation wire is returned to the distal end side. Then, when the bending lever returns to the original position, all of the pulled operation wires become loose. As a result, the bending state can be returned to the straight-line state.

In these manners, the bending lever is continuously slanted by using a small force amount, which is only enough for increasing the drag of the operation wire against the pulley. Thus, the bending portion can be bent easily by a desired amount in a desired direction. Therefore, the load on the user operating the bending lever can be significantly reduced.

When the bending state of the bending portion is maintained, the pulling force from the pulley is caused on the operation wire corresponding to the bending direction. As a result, only parts of the force on the operation wire are put on the bending lever. Thus, the load on the user holding the bending lever can be significantly reduced.

In this embodiment, the operational example has been described where the bending portion 22 is bent by slanting the bending lever 31 in the direction indicated by the arrow Y2 to pull and move the operation wire 33 for the up-direction fixed to the arm portion 36a of the arm member 36. However, the bending portion can be bent in a desired direction by slanting the bending lever 31 in the direction indicated by the arrow Y1, the arrow X1 or the arrow X2 and, as a result, by pulling or loosely moving the operation wire corresponding to the slanting operation of the bending lever like the above-described operation.

In addition, by slanting the bending lever 31 in a middle direction between the direction indicated by the arrow Y2 and the direction indicated by the arrow X2, for example, and, as a result, by moving multiple operation wires corresponding to the slanting operation like the above-described operation, the bending portion can be bent in a desired direction.

Furthermore, the form of the operating portion 24 is not limited to the above-described substantial h-form. In other words, the position of the grasping portion 25 provided in the operating portion 24 is not limited to the position in the above-described embodiment.

Figure 12:
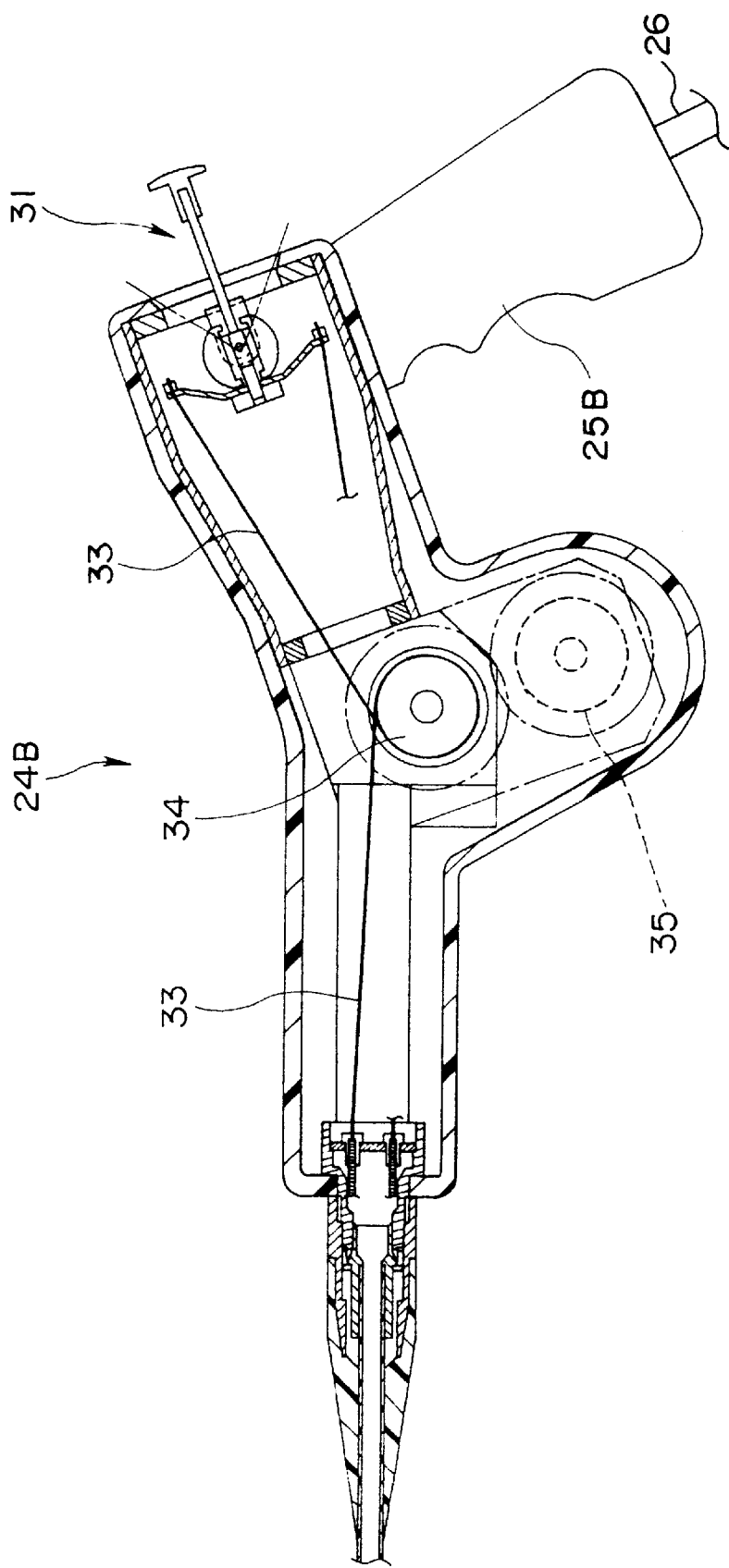
FIG. 12 is a diagram for explaining another construction of an operating portion.
Figure 13:
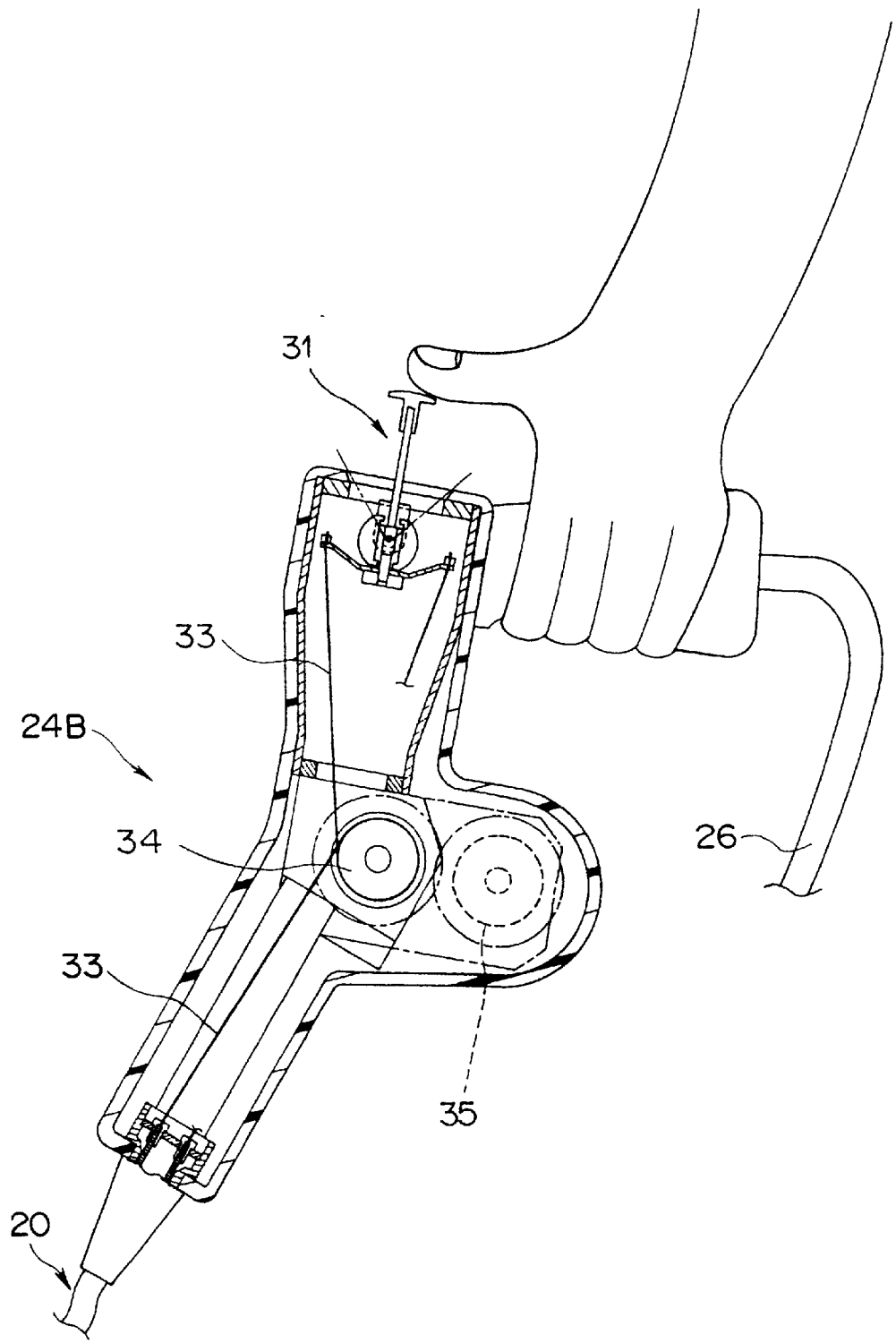
FIG. 13 is a diagram for explaining an operation state of the bending device.

Therefore, if an arrangement is possible where all of the operating wires 33 can be the slide state with respect to the pulley 34 rotated by the motor 35 when the bending lever 31 is located in a neutral state, which is an initial state, and when the pulling state of the operation wire 33 corresponds to the slanting operation on the bending lever 31, the operating portion 24A in which the grasping portion 25A is located may be constructed. Alternatively, the operating portion 24B may be constructed such that the inserting axis of the inserting portion 20 and the axis of the grasping portion 25B can cross as shown in FIG. 12. Here, the grasping portion 25B can be grasped by leaving the arm down as shown in FIG. 13. in addition, the bending lever 31 can be operated freely with the thumb of the hand grasping the grasping portion 25B. Therefore, the twisting operation on the inserting portion 20 and/or the bending operation on the bending portion 22 can be performed freely without loads on the arm.

Figure 14:
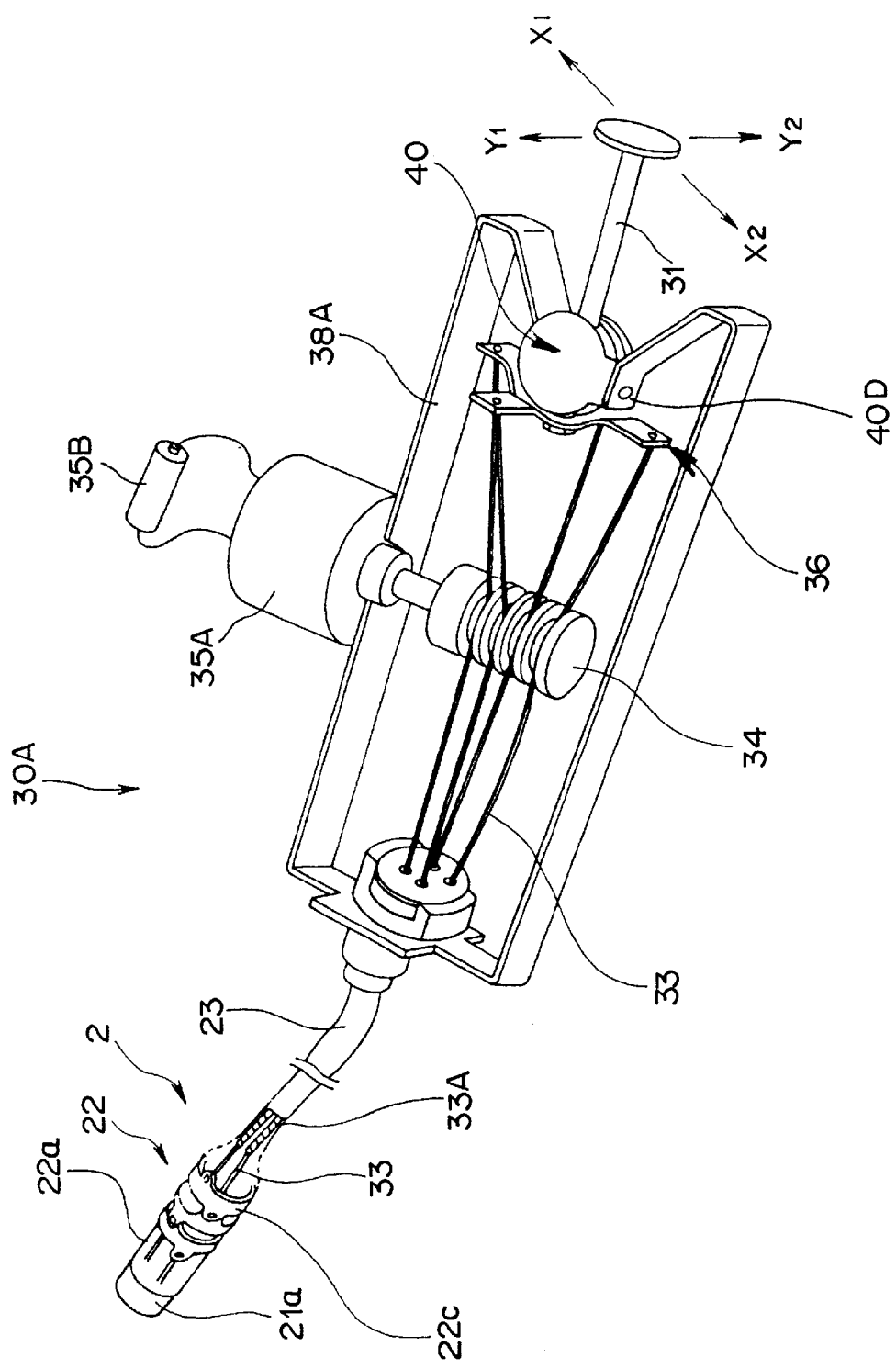
FIG. 14 is a diagram for explaining an essential part of a bending device having another construction.

In order to construct the operating portion 24B in which the grasping portion 25B is located as shown in FIG. 12, a motor 35A is coaxially provided thereto for the pulley 34 included in a bending device 30A as shown in FIG. 14. Then, the pulley 34 may be rotated by the motor 35A directly. In order to construct the bending device 30A shown in FIG. 14, a straight frame 38A is used instead of the bending frame 38 used in the bending device 30. Then, the base end portions of the bending lever 31, the bearing 40, the pulley 34 and the flexible tube portion 23 are substantially aligned in the straight frame 38A. A reference numeral 35B indicates a battery for a motor. The other arrangement is the same as the above-described embodiment, and the same reference numerals are given to the same members, whose description is omitted.

Also in the bending device 30A in the construction, by manipulating the bending lever 31 in the directions indicated by the shown arrows X1–X2, the arm portion 36 is rotated with respect to the circular axis 41 in the directions X1–X2. By manipulating the bending lever 31 in the directions indicated by the shown arrows Y1–Y2, the arm portion 36 is rotated with respect to the axis portion 40D including the first sphere bearing 42 and the second sphere bearing 43 in the directions Y1–Y2. In other words, with the rotation of the arm portion 36, the operation wire 33 fixed to the arm portion 36 is pulled or loosened.

Figure 15A:
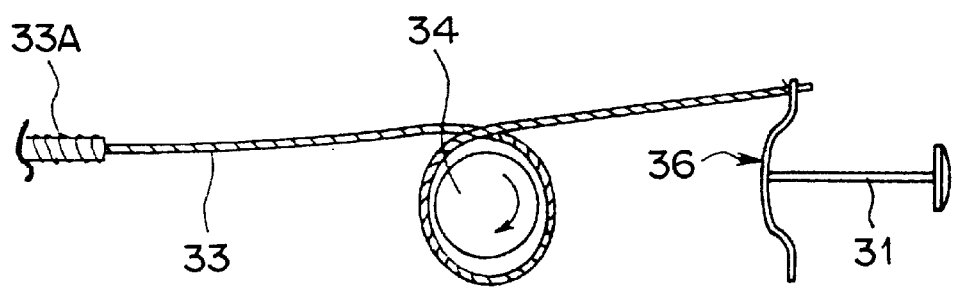
FIG. 15A is a diagram showing a state where the traction member is wound in a predetermined loose state.

More specifically, as shown in FIG. 15A when the bending lever 31 is located at the substantial center position, that is when no pulling force is applied to the operation wire 33 mounted to the arm portion 36, the winding around the pulley 34 is loose. As a result, the rotational force of the pulley 34, which is rotationally driven clockwise in the figure, for example, by the motor 35A is not transmitted to the operation wire 33.

Figure 15B:
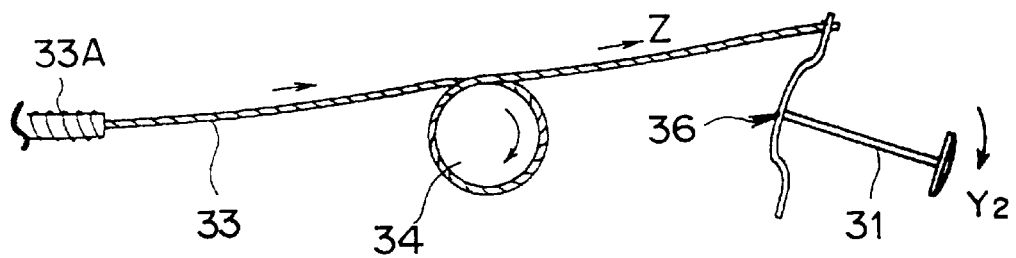
FIG. 15B is a diagram showing a state where the traction member is moved by the rotation of a pulley.

On the other hand, as shown in FIG. 15B, when the bending lever 31 is manipulated in the direction Y2 in the figure, the arm portion 36 is slanted with respect to the bearing 40. Then, the operation wire 33 is pulled in the direction Z in the figure and is wound around the pulley 34. Then, the drag between the pulley 34 and the operation wire 33 is increased. Thus, force from the rotational clockwise driving of the pulley 34 is applied to the operation sire 33. Then, the operation wire 33 is pulled and is moved in the direction indicated by an arrow Z by the rotation of the pulley 34.

In other words, like the above-described embodiment, regardless of the position of the bending lever 31, the bending portion 22 is bent by slanting the bending lever 31, like the above-described embodiment.

The axis of the grasping portion may be twisted at a predetermined degree and be slanted so as to cross a horizontal surface including the inserting axis of the inserting portion 20. The above-described embodiment has been described by using the traction-member operating device as a bending device for bending he bending portion. However, the traction-member operating device is not limited to the bending device. For example, it may be applied for a traction-member operating device provided in a crashed stone basket for gathering crashed stones, for example, by being inserted to a body cavity through an endoscope. Furthermore, the four-direction bending operation has been described as an example for the above-described endoscope. However, the same construction can be implemented for a two-direction bending operation. While friction force has been caused in the four operation wires by using one motor and one pulley, a construction is possible for operating for each of up and down and right and left by using two motors and pulleys. In the same manner as that a motor rotationally drives when an operator touches the bending lever including a touch sensor circuit, the power supply of the motor can be turned on/off.

Here, a specific construction example of an operating portion of an endoscope will be described with reference to FIGS. 16 and 17.

Figure 16:
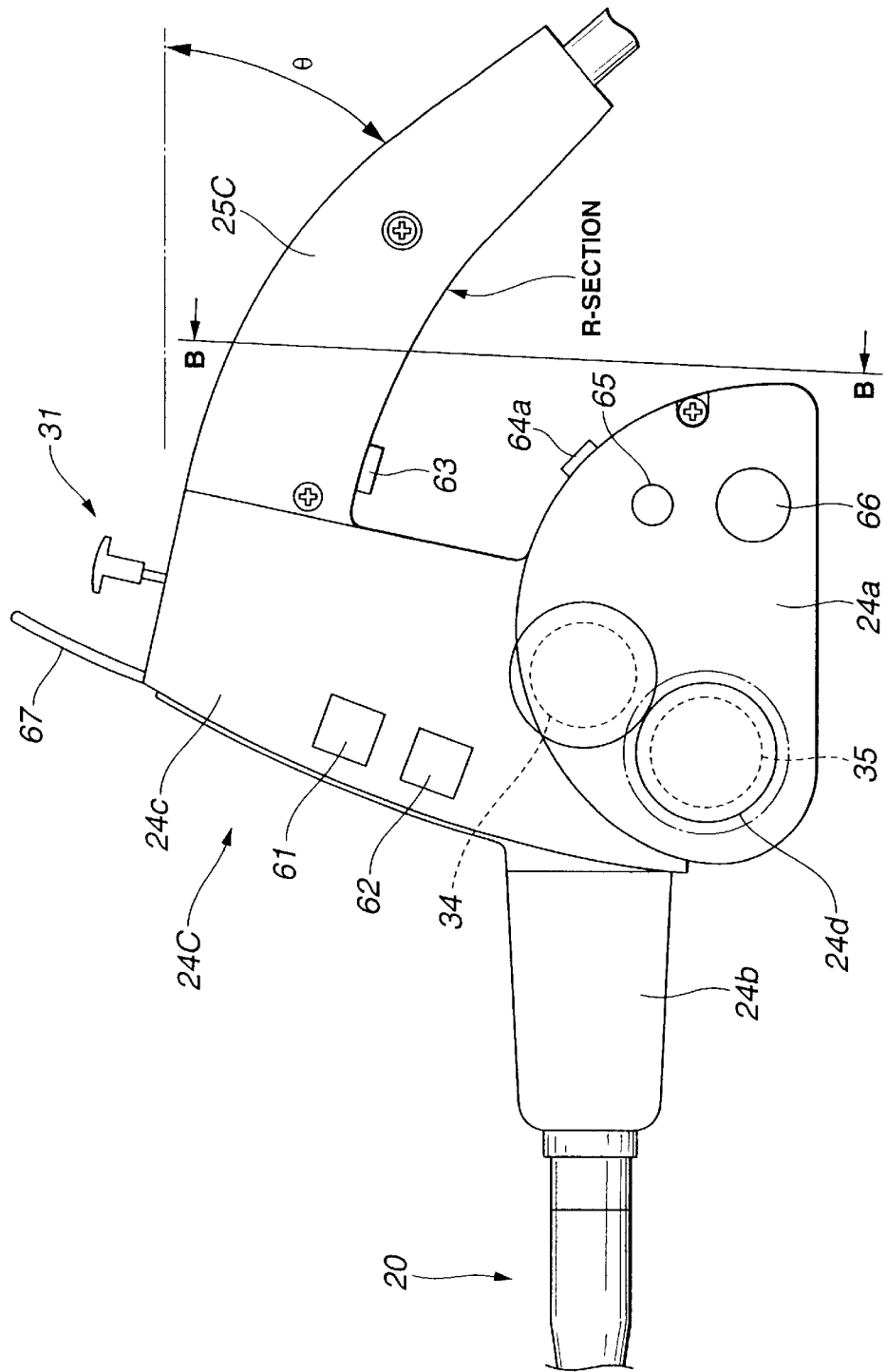
FIG. 16 is an elevation diagram for explaining a specific construction of an operating portion of the electric bending endoscope.
Figure 17:
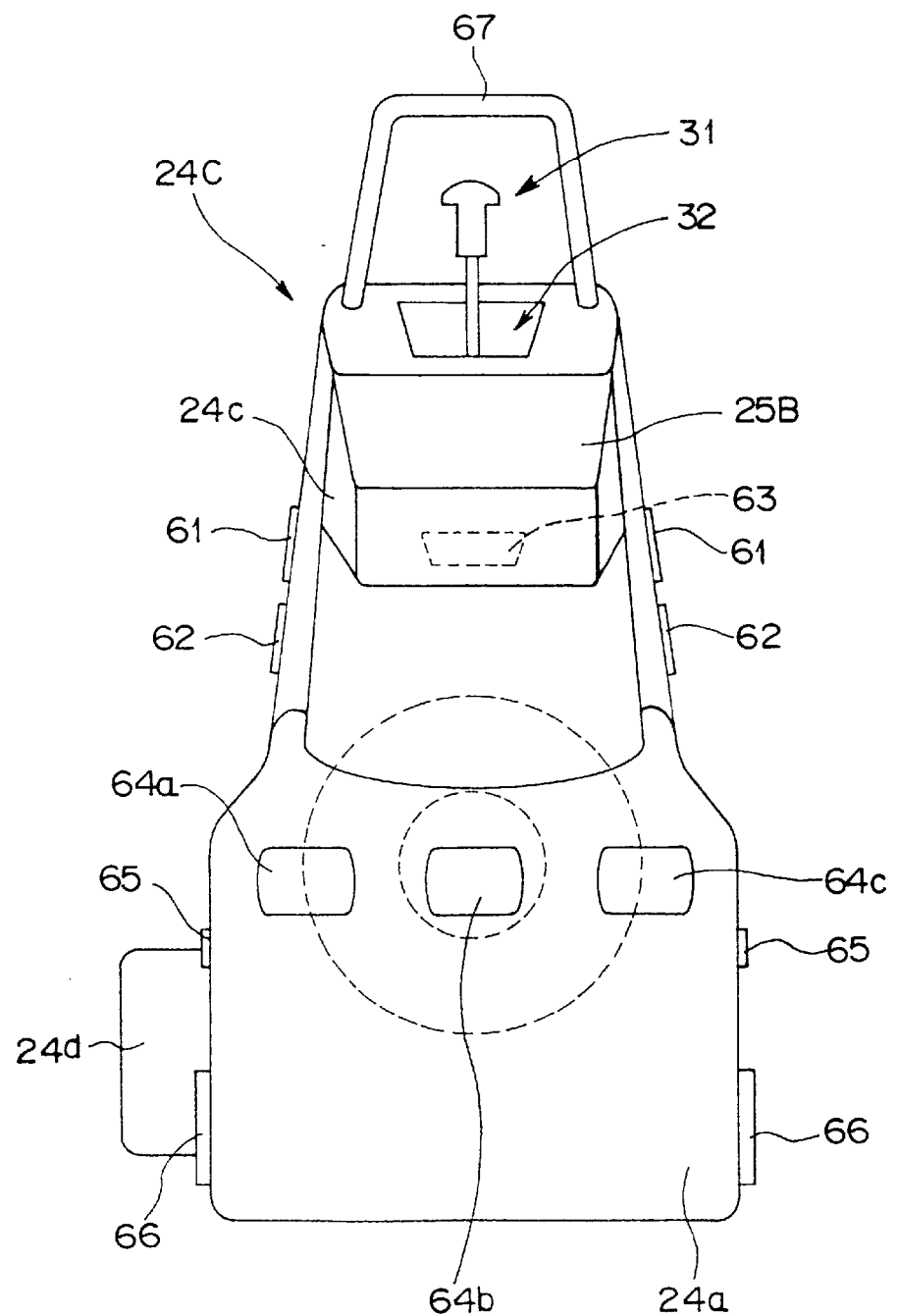
FIG. 17 is a diagram viewing the operating portion in FIG. 16 from a direction indicated by an arrow B.

As shown in FIGS. 16 and 17, in this embodiment, an operating portion 24C of the endoscope 2 includes an operating portion body 24a, an operating portion distal end portion 24b projecting from the operating portion body 24a to the distal end side, an operating portion convex portion 24c projected from the operating portion body 24a to the above side and a grasping portion 25C.

A projected motor cover portion 24d is provided in one side surface portion of the operating portion body 24a. Therefore, the motor 35 is provided in the motor cover portion 24d in this embodiment. The pulley 34 is located near the cross position of the operating portion body 24a and the operating portion convex portion 24c.

The grasping portion 25C has an axis different from the inserting axis of the inserting portion 20. The axis of the grasping portion 25 is slanted with respect to the horizontal line by a predetermined angle θ so as to cross the inserting axis of the inserting portion 20. The grasping portion 25C is formed as an R-form section in view of the grasping characteristic and the operability.

When the bending lever 31 is operated by the thumb, an image freezing switch 61 and an image recording switch 62, which can be manipulated by the index finger, for example, are provided substantially symmetrically in a side surface portion facing against the operating portion convex portion 24c of the operating portion 24C. Like the switches 61 and 62, a brightness switch 63, which can be manipulated by the index finger when the bending lever 31 is operated, is provided in the bottom surface side of the grasping portion 25C. Furthermore, multiple operation switches 64a, 64b and 64c are, for example, horizontally aligned in the back surface portion of the operating portion body 24a. An LED 65 as a pilot lump and/or a connector portion 66, which is an electric connection portion with PDA (Registered Trademark), which is one of an LCD monitor and an auxiliary device, are provided substantially symmetrically in the opposite side surface portion. A reference numeral 67 is a guard member in a substantial horseshoe-form for protecting the bending lever 31.

The image freezing switch 61 is a switch for freezing an endoscope image displayed on the monitor 3. The image recording switch 62 is a switch for instructing to record an endoscope image displayed on the monitor 3. The brightness switch 63 is a switch for adjusting brightness of an endoscope image displayed on a screen of the monitor 3. By changing a target value of auto exposure control (abbreviated as AE control, hereinafter) the brightness adjustment can be switched in eight levels, for example.

More specifically, in the brightness switch 63, a first level is set as the darkest, and the eighth level is set as the brightest. Then, the target value control is performed by turning OFF the slow shutter for the first to fifth levels. The AE control is performed by using the slow shutter for the sixth to eighth levels. The maximum exposing time is extended in order of the sixth, seventh and eighth levels. A maximum value is set for the AE target value after the fifth level.

In other words, the AE target value is increased enough up to one level before the slow-shutter operable level. When enough brightness is not obtained at the fifth level, it is moved to the sixth level such that the slow shutter can work and the endoscope image is brightened. If one brightness switch 63 is provided, a rotary switching method is adopted for switching the switch for each operation in order of 1→2→, ..., 7→8→1→2→, ... When two switches can be provided, an UP function and a DOWN function are assigned to the switches, respectively. Thus, the levels of the brightness can be switched vertically as desired.

The relationship between the switch arrangement and the functions are not limited to the above-described forms. While, in this embodiment, the switches 61m 62, 63 and 64 are projected from the surfaces forming the operating portion 24C so as to facilitate the identification by the finger. However, in addition to the switches 61, 62, 63 and 64, the LED 65 and the connector portion 66 can be placed at the same surface level or can be dented.

Figures 18A, 18B:
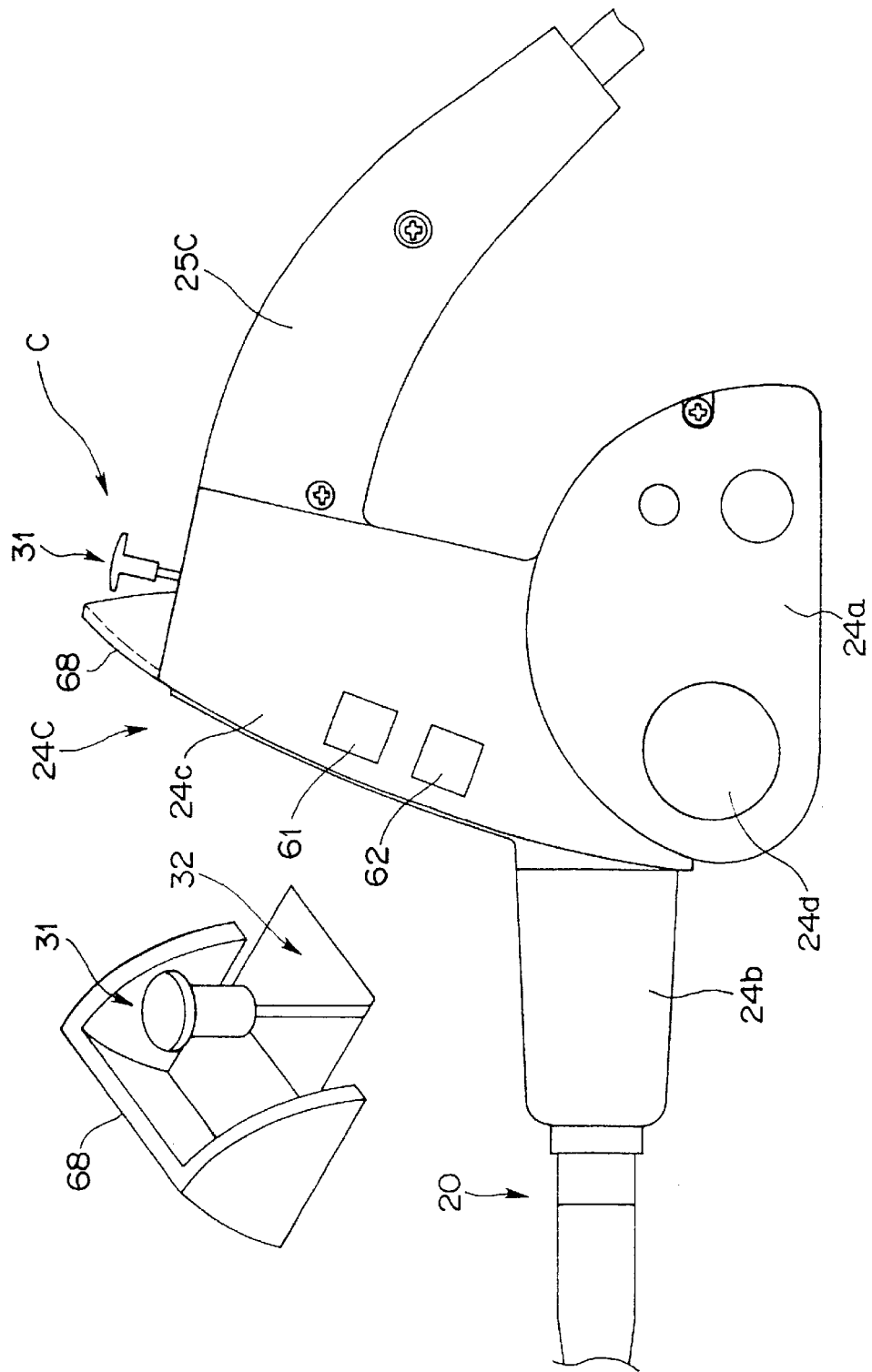
FIG. 18A is a diagram for explaining an operating portion to which a plate-shape guard member surrounding a distal end side of the bending lever is provided.
FIG. 18B is a magnified view of a part indicated by an arrow C in FIG. 18A.

As shown in FIGS. 18A and 18B, the guard member may be a plate-like guard member 68 surrounding the distal end side of the bending lever 31.

In this embodiment, the monitor 3, which is a display device, is provided to the operating portion 24C of the endoscope 2 removably. More specifically, as shown in FIGS. 19A and 19B, for example, a liquid crystal monitor 70, which is a display device, is removably mounted to a mount 72 provided in a stay 71 in the operating portion 24C. The mount 72 includes a first mount 72a to which, for example, the liquid crystal monitor 70 is removably mounted, and a second mount 72b integrally fixed to an inserting portion fixing portion 71b.

Figure 20:
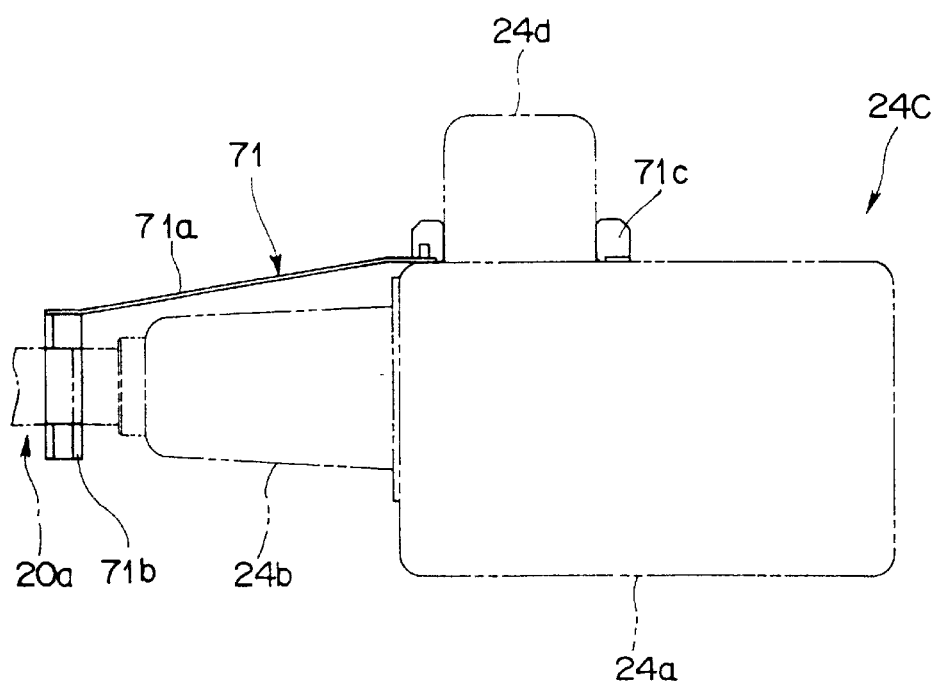
FIG. 20 is a diagram for explaining a state where a stay is attached to the operating portion.

As shown in FIGS. 19(a) and 20, the stay 71 includes a stay body 71a, the inserting portion fixing portion 71b located in a non-fold member 20a included by the inserting portion 20, and a latching ring portion 71c mounted to the motor cover portion 24d of the operating portion 24C for preventing the stay body 71a from moving back and forth toward the inserting axis. The inserting portion fixing portion 71b is provided with a hook 73 formed by an elastic member for ensuring to attach or remove the stay 71 and a lock lever 74 having a rotatable cam mechanism portion, not shown, at a predetermined position of the inserting portion fixing portion 71b.

Therefore, first of all, the latching ring portion 71c is latched in the motor cover portion 24d. Under this state, the inserting portion fixing portion 71b is mounted to the non-fold member 20a. Here, they are mounted integrally by using the elastic force that the hook 73 has. The hook 73 is held by the cam mechanism portion by manipulating the lock lever 74. Thus, the stay 71 is securely located in the operating portion 24C. Next, the liquid crystal monitor 70 is mounted in the first mount 72a. Then, the liquid crystal monitor 70 is located in the operating portion 24C integrally.

Figure 21:
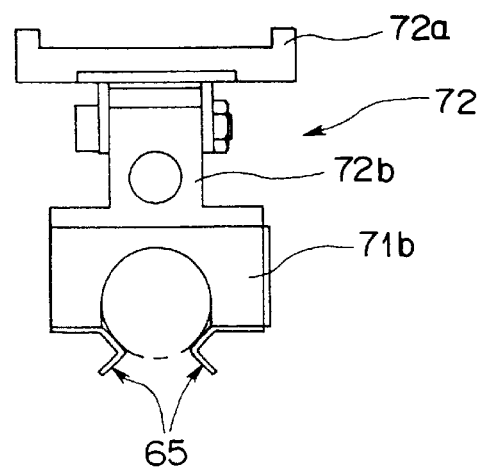
FIG. 21 is a diagram for explaining another construction of an inserting-portion fixed part.

Instead of the liquid crystal monitor 70, PDA (registered trademark) may be located in the first mount 72a. Instead of the inserting portion fixing portion 71b of the stay 71 including the hook 73 and the lock lever 74, a pair of plate springs 65, for example, having a predetermined energizing force as shown in FIG. 21. The inserting portion fixing portion 71b may be attached to the non-fold member 20a removably by using the energizing force of the plate springs 65.

An endoscope apparatus having an electric bending endoscope according to a second embodiment of the present invention with reference to FIGS. 22 to 29.

Figure 22:
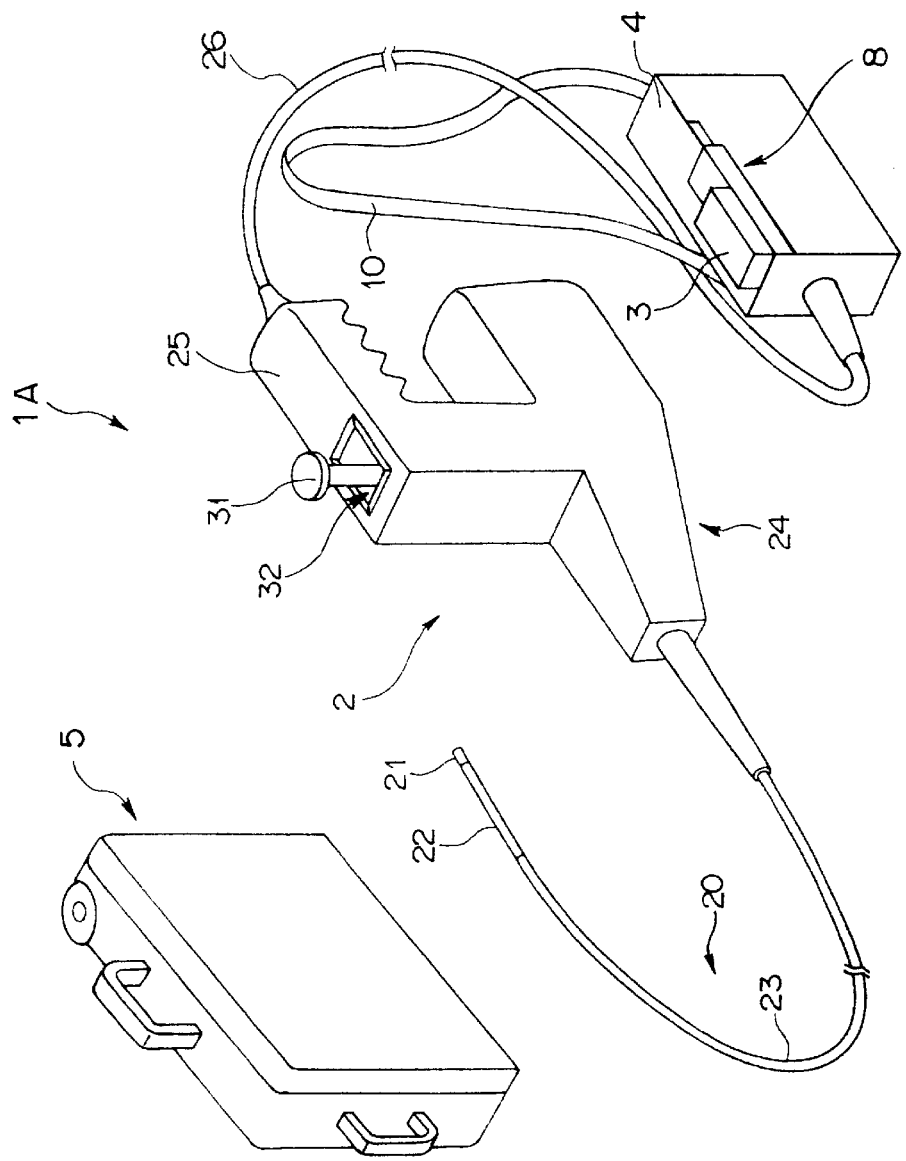
FIG. 22 is a diagram for explaining an electric bending endoscope including a mobile traction-member operating device.
Figure 23:
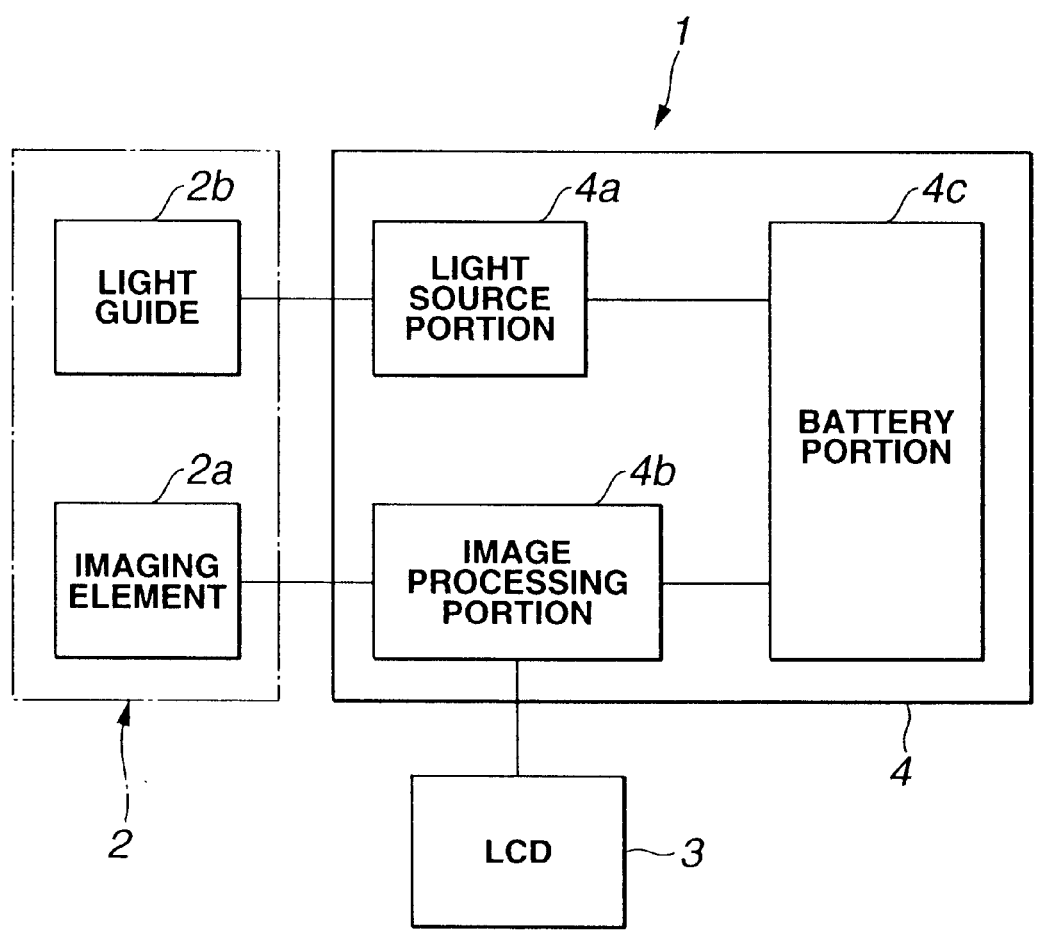
FIG. 23 is block diagram for explaining a construction of an endoscope apparatus.

As shown in FIGS. 22 and 23, an endoscope apparatus 1A of this embodiment mainly includes an apparatus body including a battery driven, industrial, for example, endoscope 2 (abbreviated as endoscope, hereinafter) in which an image pickup element 2a is self-contained in a distal end portion 21 of an inserting portion 20, a light source portion 4a for supplying illuminating light to a light guide fiber 2b, which is an illuminating optical system of the endoscope 2, for illuminating an observer part, and an image processing portion 4b for driving the image pickup element 2a and for generating a video signal from an image signal photoelectrically transduced and output by the image pickup element 2a, a liquid crystal monitor, for example, (abbreviated as LCD, hereinafter) 3, which is a below-described display device for receiving a video signal output from the image processing portion 4b and for displaying an endoscope image, and a battery portion 4c such as a dry cell or a chargeable battery for supplying power to the LCD 3, the optical source portion 4a and the image processing portion 4b and an accommodating case 5 for accommodating the apparatus body 4 and the endoscope 2. The LCD 3 in this embodiment is fixed to the apparatus body 4 integrally through the display device positioning member 8.

A reference numeral 10 indicates a belt to be used for wearing the apparatus body 4, which is mounted to the apparatus body 4 integrally in advance.

The light guide fiber 2b for supplying illuminating light, a signal cable (not shown) for transferring a drive control signal of the image pickup element 2a and an image signal photoelectrically transduced by the image pickup element 2a, and so on are inserted through the universal cord 26. One end portion of the universal cord 26 is fixed to the operating portion 24 integrally while the other end portion is fixed to the apparatus body 4 integrally. They are adjusted so as to achieve good observation of the image pickup element 2a provided in the endoscope 2 and the image processing portion 4b provided in the apparatus body 4.

The other arrangement is the same as the first embodiment, and the same reference numerals are given to the same members, whose description is omitted.

Figure 24:
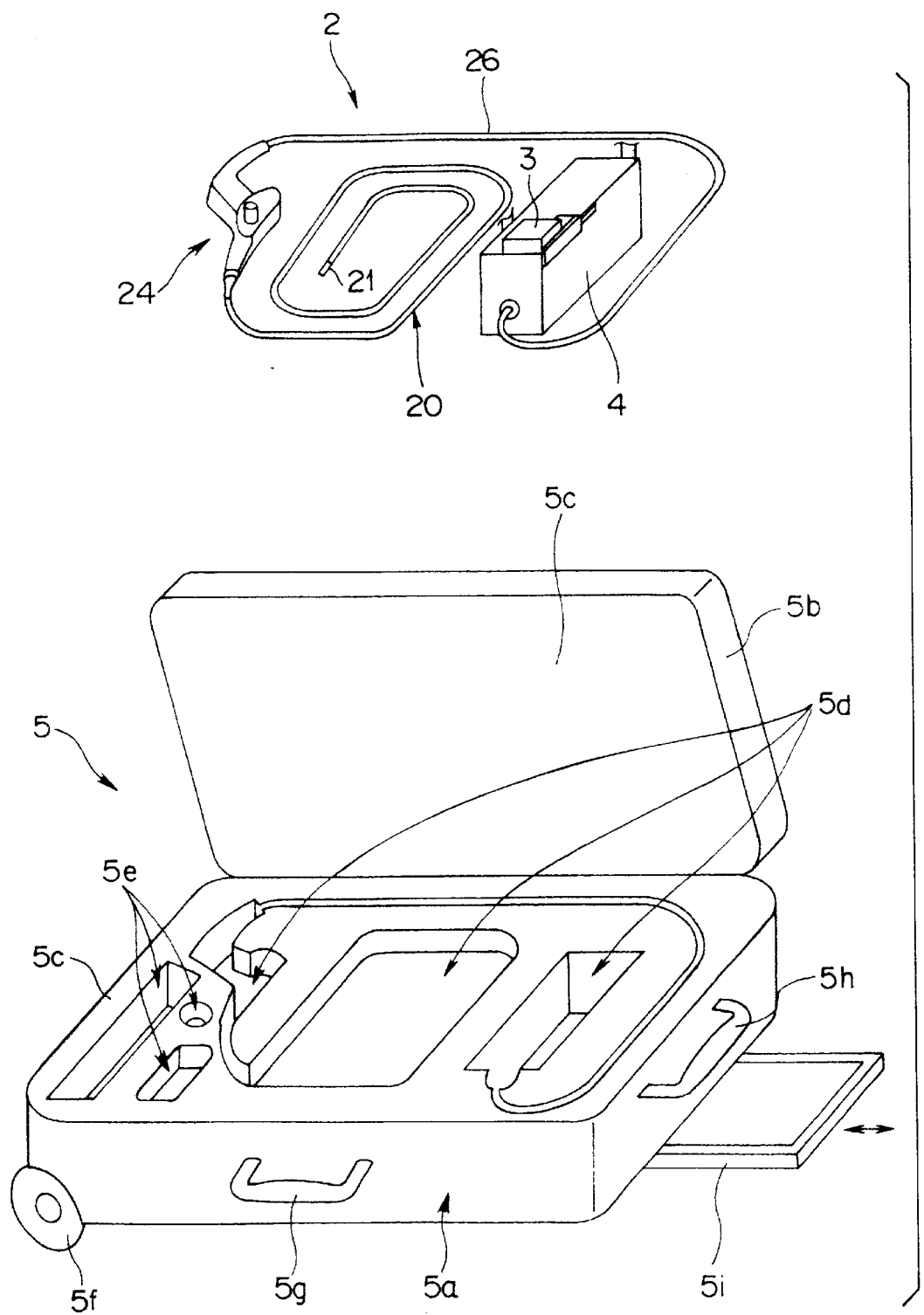
FIG. 24 is a diagram for explaining a relationship among an accommodating case, an endoscope and a device body.

As shown in FIG. 24, the endoscope 2 and the apparatus body 4 integrally connected to the endoscope 2 through the universal cord 26 are located in an accommodating concave portion 5d formed in a protection member 5c provided as an interior member in a case body 5a side of the accommodating case 5. Multiple auxiliary concave portions 5e for accommodating auxiliary tools to be used together with the endoscope 2 are formed in the protection member 5c.

A reference numeral 5b indicates a lid member, and the protection member 5c is provided also in the lid member 5b side. A reference numeral 5f indicates a caster, and a reference numeral 5g indicates a first handle. A reference numeral 5h indicates a second handle, and a reference numeral 5i indicates a stretchable third handle as shown by an arrow.

Figure 25:
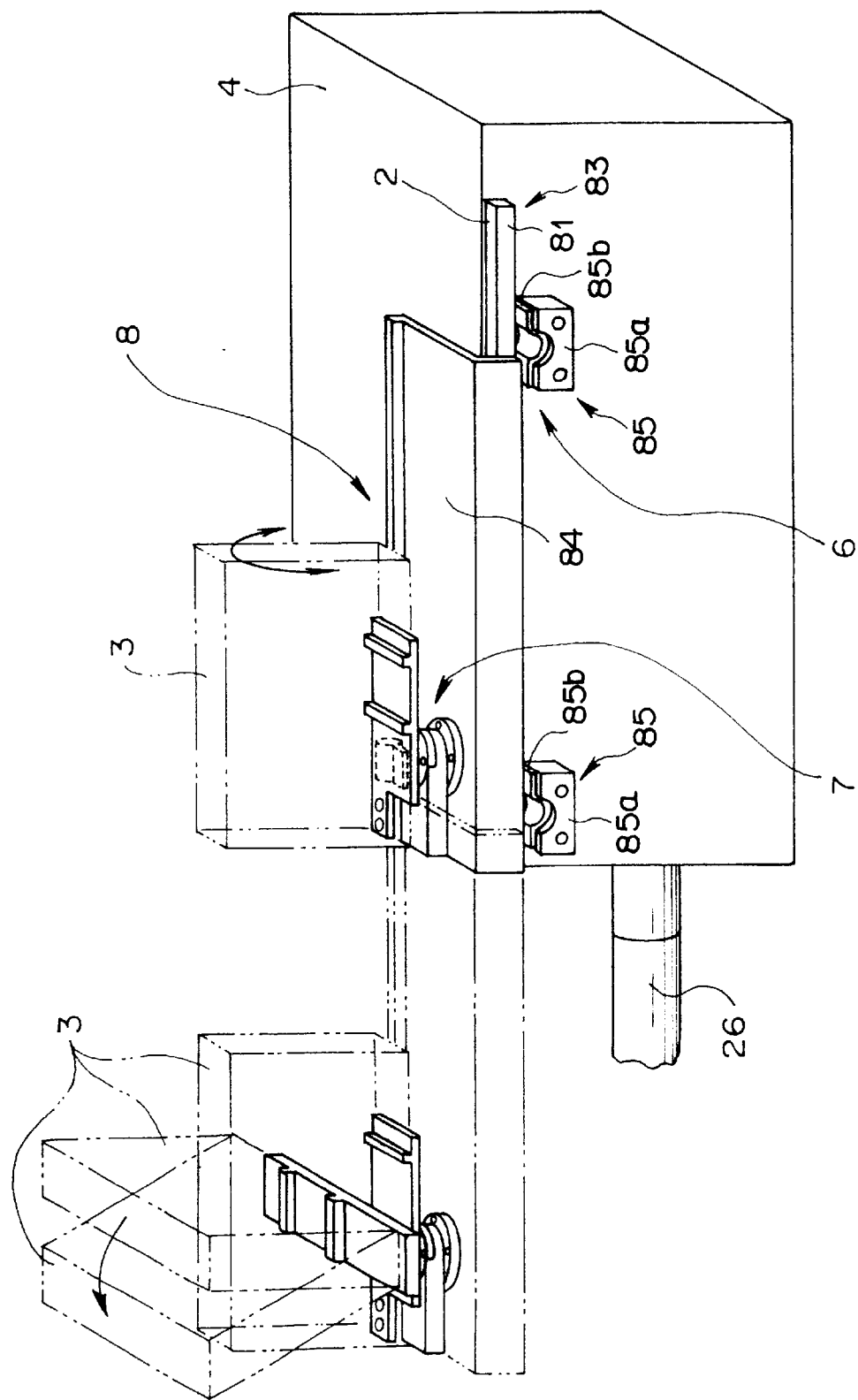
FIG. 25 is a diagram for explaining a display-device positioning member.

As shown in FIG. 25, the apparatus body 4 is provided with a display device positioning member 8 including a slide member 6, which is a sliding portion for positioning the LCD 3 slidably and a rotational member 7, which is a rotational unit for rotating and changing the direction of the display surface of the LCD 3 freely. By fixing the LCD 3 to the display device positioning member 8 integrally, the LCD 3 can be positioned to the apparatus body 4 integrally.

Figure 26:
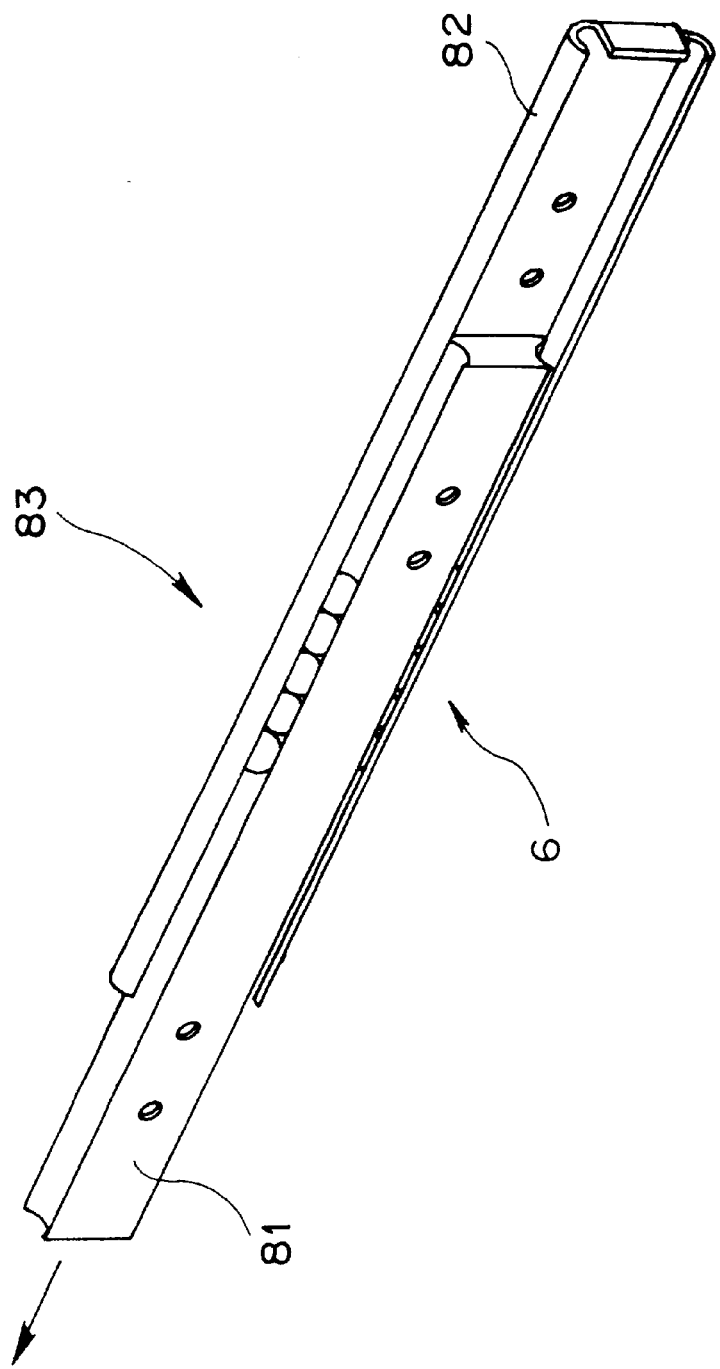
FIG. 26 is a diagram for explaining a slide member of the display-device positioning member.
Figure 27:
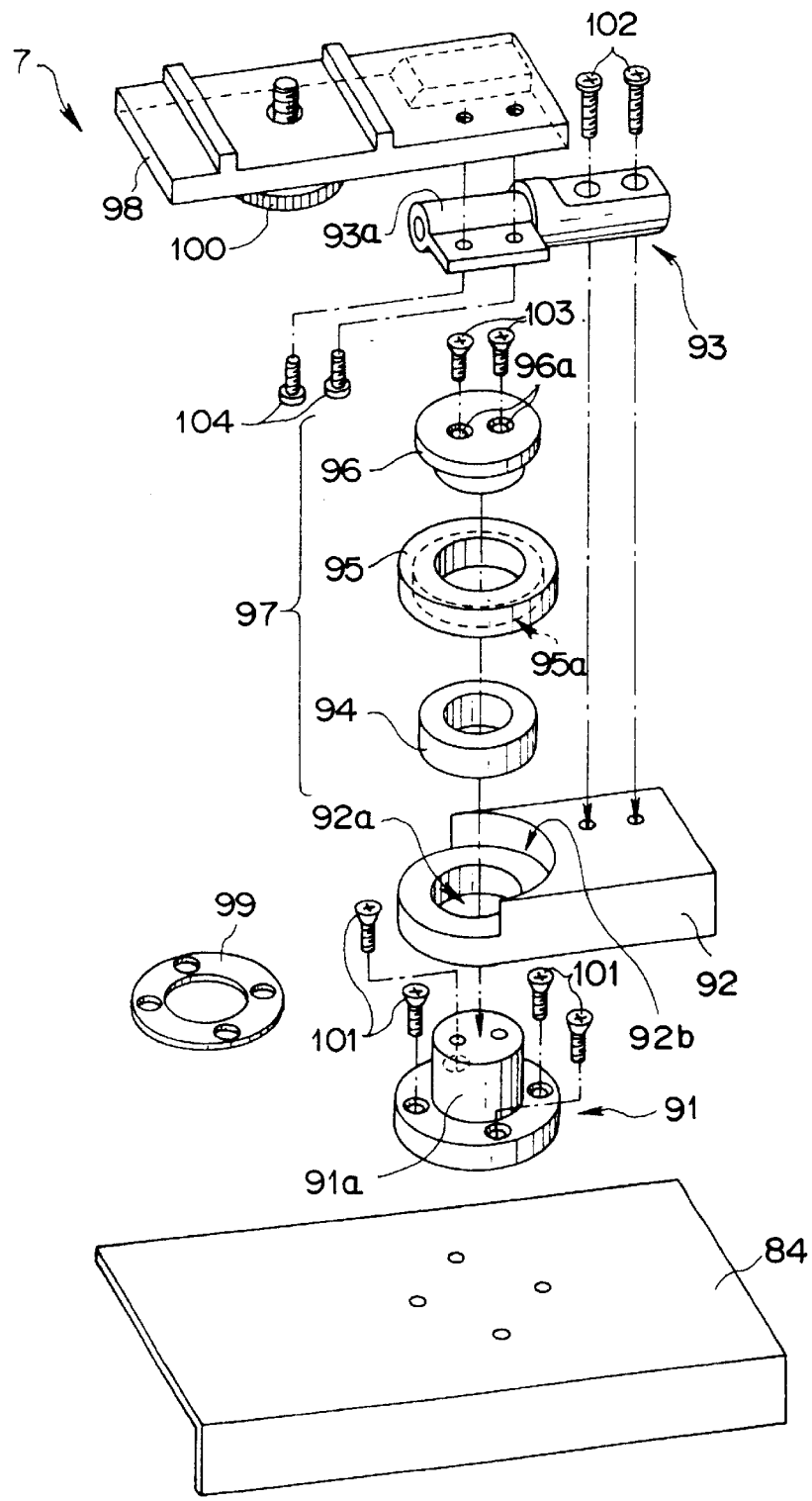
FIG. 27 is a diagram for explaining a rotating member of the display-device positioning member.

As shown in FIG. 26, the slide member 6 includes a moving member 83, which can be moved freely by combining the plate members 81 and 82, for example, and a slide plate member 84 shown in FIG. 27, which is fixed to the first plate member 81 that is a sliding member of the moving member 83.

The second plate member 82 is fixed at a predetermined position of the apparatus body 4 by using a screw, for example, substantially horizontally and integrally. A sliding member such as a ball bearing is located between the first plate member 81 and the second plate member 82 such that the first plate member 81 can be slide smoothly.

A reference numeral shown in FIG. 25 indicates a positioning member for determining a sliding position of the slide plate member 84. The positioning member 85 includes a stopper 85a having a concave portion and a plate spring 85b having a predetermined elastic force located in the stopper 85a.

On the other hand, as shown in FIG. 27, the rotational member 7 includes an axis member 92 whose section is in a substantial convex form having a convex portion 91a, a rotational plate member 92 located in the convex portion 91a rotatably, a hinge 93, which includes a rotational portion 93a and is a rotational portion in the horizontal axis direction, and a rotation adjusting member 97 having a rubber member 94, which is ring-shape, elastic member, a substantial-ring-shape fastening member 95 and a lid member 96.

The axis member 91 is screwed and is fixed to the slide plate member 84 by using a screw 101, for example. The convex portion 91a is a vertical direction axis. The rotational plate member 92 is in a plate-like form, has a through-hole 92a located in the convex portion 91a and is located to the convex portion 91a rotatably. A circular notch portion 92 concentric with the through-hole 92a is formed in the rotational plate member 92. The rotational portion 93a of the hinge 93 is fastened to the rotational plate member 92 by using a screw 102, for example. The rotational portion 93a rotates by using a predetermined force amount in the horizontal axis direction and is held in a predetermined state. The rubber member 94 is located in the circular notch portion 92b of the axis member 91 and adjusts such that the rotational plate member 92 can be held securely and can rotate by using a predetermined force amount. The fastening member 95 has a concave portion 65a in which the rubber member 94 is located. The lid member 96 has, for example, two screw holes 66a, and is located so as to block the center through-hole of the fastening member 95. That is, the rotational portion in the vertical axis direction includes the axis member 91 and the rotational plate member 92.

An LCD positioning member 98 is fastened in the rotational member 93a of the hinge 93 by using a screw 104. A reference numeral 99 is a sliding member, which is located in the convex portion 91a and prevents galling and so on due to the rotation between the axis member 91 and the rotation plate member 92. A reference numeral 100 is an LCD fixing screw for fixing the LCD 3 to the LCD positioning member 98 removably.

Then, first of all, the axis member 91 is screwed and is fixed into the slide plate member 84 by using the screw 101. Next, the through-hole 92a of the rotational plate member 92 is located to the convex portion 91a of the axis member 91. The hinge 93 is fastened to the rotational plate member 92, and the LCD positioning member 98 is integrally fixed to the hinge 93. Next, the fastening member 95 in which the rubber member 94 is located is located in the circular notch portion 92b of the rotational plate member 92. Next, the lid member 96 is fixed to the axis member 91 by using a desired fastening force.

Figure 28:
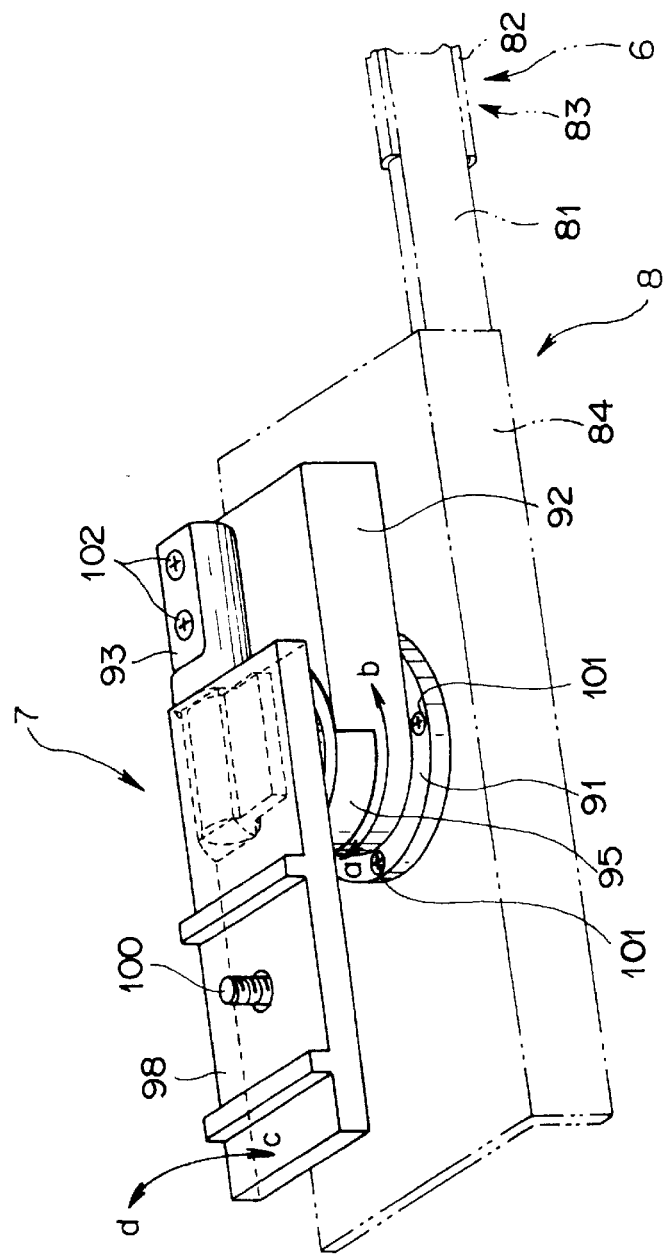
FIG. 28 is a diagram showing an assembled display-device positioning member.

Thus, the display device positioning member 8 shown in FIG. 28 is constructed. By positioning the LCD 3 in the display device positioning member 8, the LCD 3 rotates freely as indicated by arrows a and b with respect to the vertical axis direction and rotates freely as indicated by arrows c and d with respect to the horizontal axis direction. In addition, the LCD 3 moves back and forth.

An operation of the endoscope apparatus 1A constructed as described above will be described.

First of all, a user brings the accommodating case 5 to a place for observation. After bringing the accommodating case 5 to the observation place, the endoscope 2 and the apparatus body 4, which are constructed integrally, are taken out from the accommodating case 5. After that, the belt 5 is hung over the shoulder, for example, to hang the apparatus body from the shoulder.

Figure 29:
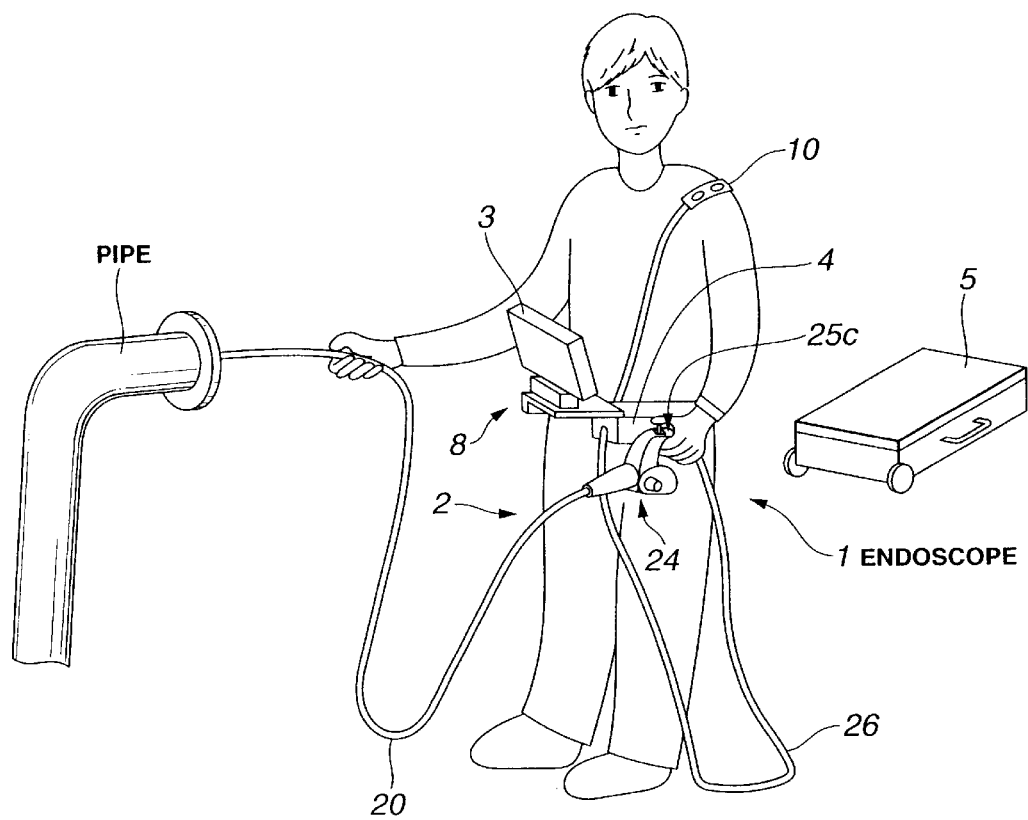
FIG. 29 is a diagram for explaining an example of a state where the electric bending endoscope is used.

Next, the user adjusts the screen of the LCD 3 located in the apparatus body 4 at an easy-to-view position. Here, the slide member 6 and the rotational member 7 of the display device positioning member 8 are adjusted properly. Thus, the LCD 3 is located at a desired easy-to-view position as shown in FIG. 29.

Next, the user grasps the grasping portion 25C of the operating portion 24C by his/her left hand and grasps the inserting portion 20 by his/her right hand. The user inserts the inserting portion 20 toward a target part within a pipe, for example, by observing an endoscope image displayed on a screen of the LCD 3 at the same time.

In this way, by integrally providing the display device to the apparatus body through the display device positioning member including the slide member and the rotational member, the located position of the LCD, for example, which is a display device can be adjusted freely so as to perform endoscope observation in a good observation condition at all times.

The endoscope, the endoscope apparatus and the display device are constructed integrally, and the light source portion and the image processing portion are provided to the apparatus body. In addition, a battery for supplying power to the light source portion, the image processing portion and the display device is provided therein. The accommodating case for accommodating the endoscope, the apparatus body and the display device is prepared. Thus, after bringing the accommodating case to an examined location, the endoscope and the apparatus body, which are constructed integrally, is taken out from the accommodating case. Then, the endoscope observation can be performed immediately.

Figure 30:
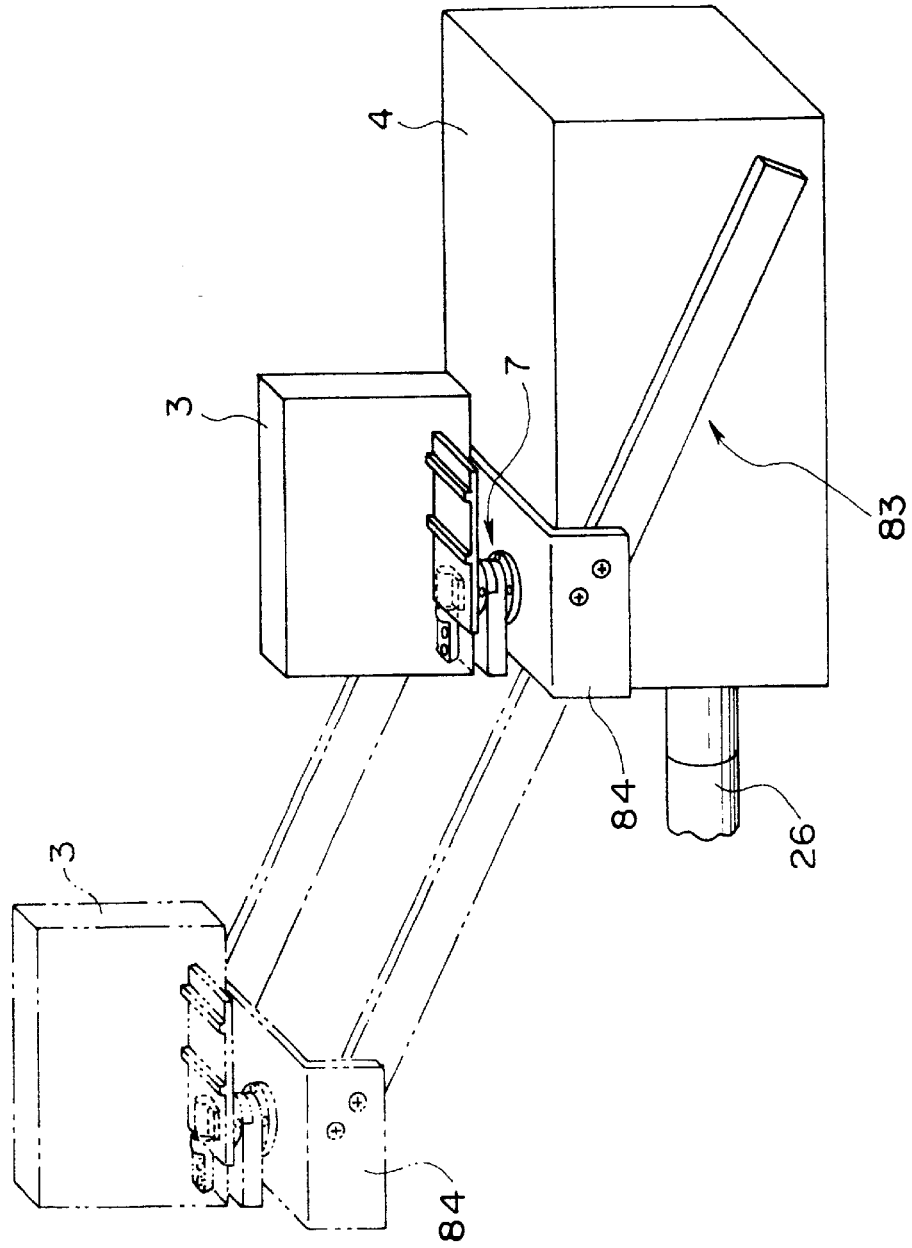
FIG. 30 is a diagram for explaining a construction in which the slide member is slantingly located in the apparatus body.

By locating the moving member 83 included in the slide member 6 diagonally with respect to the apparatus body 4 as shown in FIG. 30, the located position of the LCD 3 may be adjusted freely so as to perform good observation like the above case.

Figure 31:
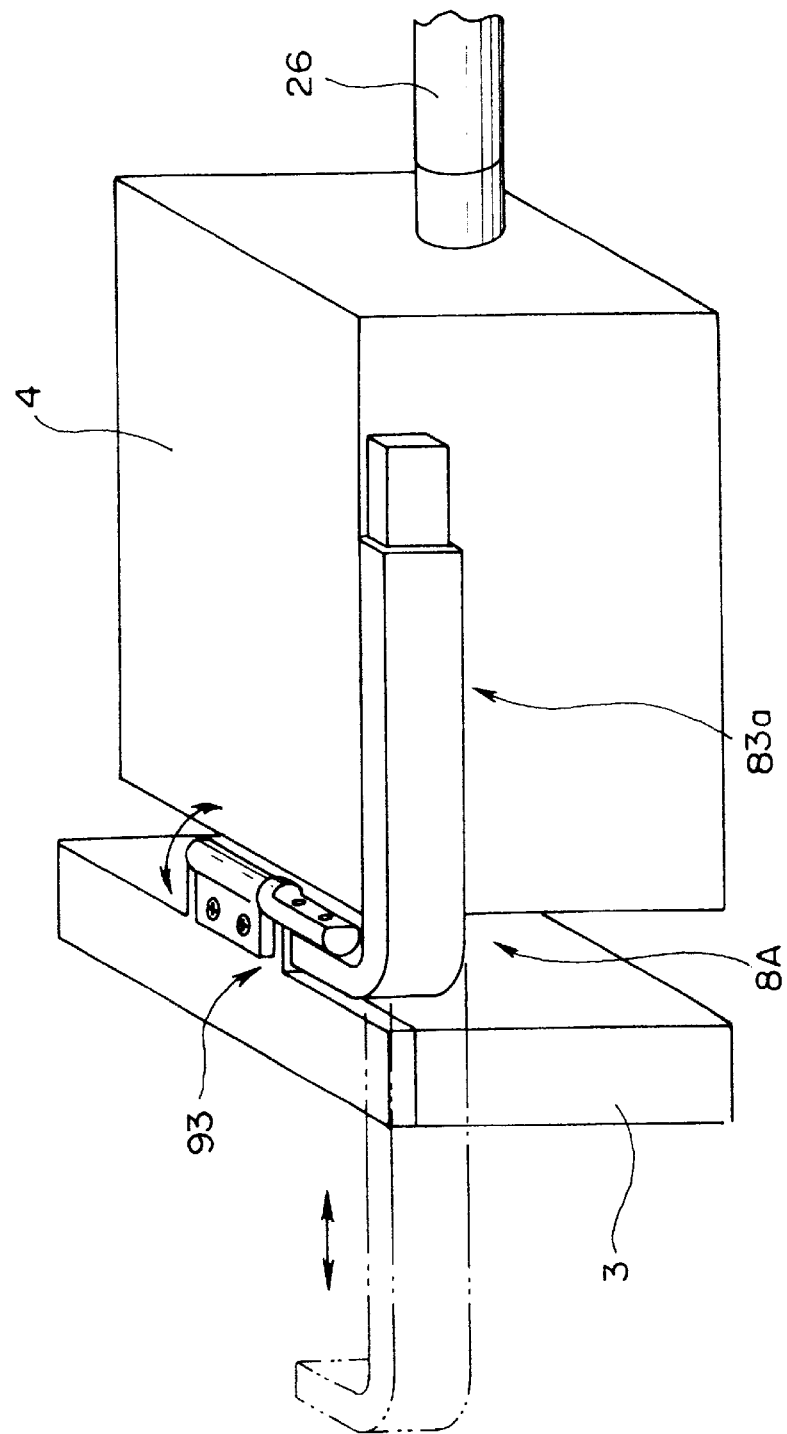
FIG. 31 is a diagram for explaining another construction of a display-device positioning member.
Figure 32:
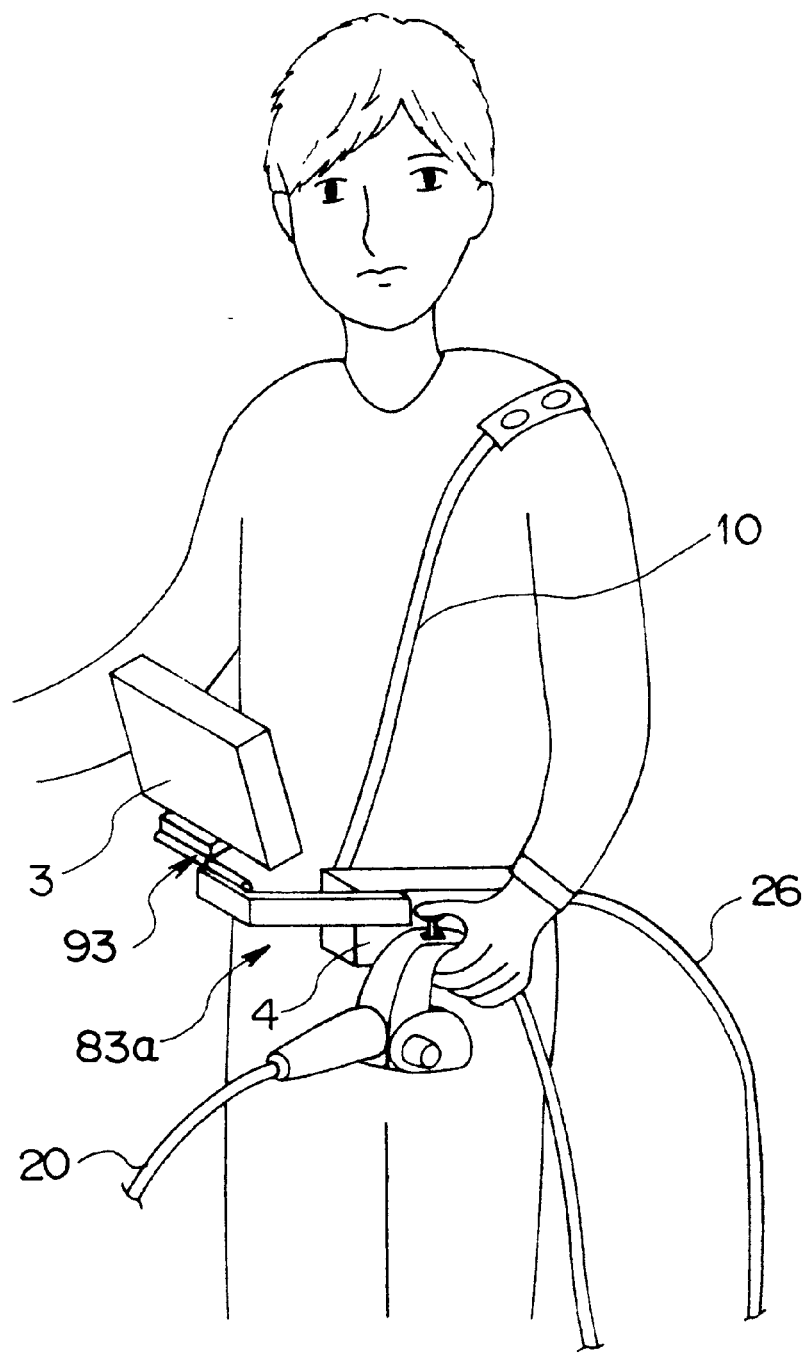
FIG. 32 is a diagram for explaining a state where the display-device positioning member in FIG. 31 is used.

The hinge 93 for rotating the LCD 3 in the horizontal axis direction as shown in FIG. 31 may be provided in the front side of the moving member 83a so as to construct the display device positioning member BA. Thus, in a condition before use, the LCD 3 may be located in the front surface side of the apparatus body. In this case, the universal cord 26 extends from the base end side of the apparatus body 4. Therefore, the working condition as shown in FIG. 32 can be obtained.

In addition, as shown in FIG. 33A, by providing the moving member 83b in the opposite side of the apparatus body 4 and by linking the moving member 83b, the slide plate member 84 and a second hinge 93A, the LCD 3 fixed to the slide plate member 84 can rotate as indicated by an arrow e or f.

Thus, the LCD 3 is located in the front position side of the user as shown in FIG. 33B so that an endoscope image can be observed.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electric bending endoscope having a traction-member operating device including:
    traction members each of whose one end portion is fixed to and extends from a distal end portion of a long and narrow inserting portion;
    a pulley forming multiple peripheral recesses in which middle parts of the traction members are wound and are located in predetermined states, respectively;
    driving means for rotating the pulley in a predetermined direction;
    an arm member having a plurality of arm portions to which base end portions of the traction members wound and located in the peripheral recesses of the pulley and extended therefrom are fixed; and
    an operation instructing lever to which the arm member is integrally fixed and having an operating portion for changing a slanting direction and a slanting amount to instruct to move a predetermined traction member from the plurality of traction members by a predetermined amount.

2. An electric bending endoscope according to claim 1, wherein an angle formed by the traction member extending from the pulley to the distal end portion and the traction member extending from the pulley to the arm member is set between 10 degree to 180 degree.

3. An electric bending endoscope according to claim 1, wherein a buffer member for generating frictional force, which is fixed to the traction members rotatably with respect to the pulley is provided between the pulley and the traction member.

4. An electric bending endoscope according to claim 1, wherein a pair of a first slanting-state adjusting member and a second slanting-state adjusting member for adjusting a maximum slanting operation range of the operation instructing lever is movably provided around the operation instructing lever.

5. An electric bending endoscope according to claim 1, wherein a grasping portion having an axis different from an inserting axis of the inserting portion is provided in the operating portion.

6. An electric bending endoscope according to claim 5, wherein the operation instructing lever is located in a distal end side of the grasping portion.

7. An electric bending endoscope according to claim 5, wherein the axis of the grasping portion is slanted by a predetermined angle and is crossed with the inserting axis of the inserting portion.

8. An electric bending endoscope according to claim 1, wherein a display device is removably provided in the operating portion.

9. An electric bending endoscope according to claim 8, wherein the display device is PDA.

10. An electric bending endoscope according to claim 1, further comprising:
    an apparatus body having an image processing portion for generating a video signal from an image signal output from an image pickup element integrally included in the electric bending endoscope, a light source portion for supplying illuminating light for illuminating a light guide included in the electric bending endoscope, and a battery for supplying power to the image processing portion, the light source portion, and the driving means; and
    a display device positioning member for movably positioning a display device for receiving a video signal output from the image processing portion and for displaying an endoscope image.

11. An electric bending endoscope according to claim 10, wherein the display device positioning member comprises:
    a sliding portion for moving the display device in a longitudinal direction of the apparatus body;
    a vertical-axis-direction rotating portion for rotating a direction of a display surface of the display device in a vertical axis direction; and
    a horizontal-axis-direction rotating portion for rotating in a horizontal axis direction.

12. An electric bending endoscope according to claim 10, further comprising a display device located on the apparatus body and an accommodating case for accommodating the electric bending endoscope, which is integrated to the apparatus body.

* * * * *